(12) United States Patent
Matsui et al.

(10) Patent No.: US 7,427,671 B1
(45) Date of Patent: Sep. 23, 2008

(54) COMPOSITIONS OF ALPHA PLATELET DERIVED GROWTH FACTOR RECEPTOR NUCLEIC ACID AND PROTEIN AND METHOD OF MAKING

(75) Inventors: Toshimitsu Matsui, Rockville, MD (US); Stuart A. Aaronson, Great Falls, VA (US); Jacalyn H. Pierce, Bethesda, MD (US)

(73) Assignee: The United States of America as represented by the Secretary, Department of Health and Human Services, Washington, DC (US)

( * ) Notice: Subject to any disclaimer, the term of this patent is extended or adjusted under 35 U.S.C. 154(b) by 0 days.

(21) Appl. No.: 08/439,095

(22) Filed: May 11, 1995

Related U.S. Application Data

(63) Continuation of application No. 07/915,884, filed on Jul. 20, 1992, now abandoned, which is a continuation of application No. 07/308,282, filed on Feb. 9, 1989, now abandoned.

(51) Int. Cl.
*C07K 14/71* (2006.01)
*C07H 21/04* (2006.01)
*C12N 15/12* (2006.01)

(52) U.S. Cl. .................... 530/395; 536/23.5; 435/70.1

(58) Field of Classification Search ............... 435/6, 435/7, 69.1, 69.4, 7.1, 320.1; 530/399, 827; 536/27, 23.1, 24.1, 24.3–24.33; 436/501, 436/536, 87, 815; 935/13, 15, 23, 78, 77
See application file for complete search history.

(56) References Cited

U.S. PATENT DOCUMENTS

| | | | |
|---|---|---|---|
| 4,766,073 A | 8/1988 | Murray et al. | 435/172.3 |
| 5,094,941 A | 3/1992 | Hart | 435/7.9 |
| 5,100,774 A | 3/1992 | Rakowicz-Szulczynska | 435/6 |
| 5,219,727 A | 6/1993 | Wang et al. | 435/6 |
| 5,371,205 A | 12/1994 | Kelly et al. | 536/23.5 |
| 5,567,584 A * | 10/1996 | Sledziewski et al. | 435/6 |
| 6,043,211 A | 3/2000 | Williams et al. | |
| 6,110,737 A | 8/2000 | Escobedo et al. | |
| 6,372,438 B1 * | 4/2002 | Williams et al. | 435/7.1 |

FOREIGN PATENT DOCUMENTS

EP    327 369    8/1989

OTHER PUBLICATIONS

Gronwald et al. (1988) Proc. Natl Acad. Sci (USA) vol. 85, pp. 3435-3439.*
Heldin et al. (1988) The EMBO Journal, vol. 7, No. 5, pp. 1387-1393.*
Raines et al. (1982) Journal of Biological Chemistry, vol. 257, No. 9, pp. 5154-5160.*
New England Biolabs 1986/87 Catalog (publ. by New England Biolabs, Beverly, Massachusetts, USA) pp. 60 and 61 and 62.*
Y. Yarden et al. "Structure of the receptor for platelet-derived growth factor helps define a family of closely related growth factor receptors", *Nature*, 323:226-32 (1986).
Hart, et al.; "Two Classes of PDGF Receptor Recognize Different Isoforms of PDGF" Science 240:1529-31 (Jun. 10, 1988).
Kruh, et al.; "A Novel Gene Closely Related to the *abl* Proto-Oncogene" Science 234: 1545-1548 (Dec. 19, 1986).
King, et al.; "Amplification of a Novel v-*erb*B-Related Gene in a Human Mammary Carcinoma" Science 229: 974-976 (Sep. 6, 1985).
Betsholtz et al., "Coexpression of a PDGF-Like Growth Factor and PDGF Receptors in a Human Osteosarcoma Cell Line: Implications for Autocrine Activation" *Cell*, 39: 447-457 (1984).
Matsui et al., "Isolation of A Novel Receptor cDNA Establishes the Existence of Two PDGF Receptor Genes" *Science*, 243: 800-804, (1989).
Miki et al., "An Efficient Directional Cloning System to Construct cDNA Libraries Containing Full-Length Inserts at High Frequency" *Gene*, 83(1) : 137-146 (1989).
Giese et al., The Role of Individual Cysteine Residues in the Structure and Function of the *v-esis* Gene Product, *Science*, 236: 1315-1318 (1987).
Claesson-Welsh et al., cDNA Cloning and Expression of a Human Platelet-Derived Growth Factor (PDGF) Receptor Specific for β-type Chain PDGF Molecules, a *Mol. Cell, Biol*, 8(8): 3476-3486 (1988).
Claesson-Welsh et al., "cDNA Cloning and Expression of a Human A-Type Platelet-Derived Growth Factor (PDGF) Receptor Establishes Structural Similarity to the B-Type PDGF Receptor," *PNAS*, (USA), 86(13): 4917-4921 (1988).
Claesson-Welsh et al. Identification and Structural Analysis of the A Type Receptor for Platelet-derived Growth Factor, *J. Biol. Chem.*, 264: 1742-1747 (1989).
Nister et al. "Expression of Messenger RNAs for Platelet-derived Growth Factor and Transforming Growth Factor-α and Their Receptors in Human Malignant Glioma Cell Lines," *Can. Res.*, 48: 3910-3918 (1988).
Ronnstrand et al. Characterization of Two Monoclonal Antibodies Reactive with the External Domain of the Platelet-derived Growth Factor Receptor, *J. Biol. Chem.*, vol. 263 (1988); 10429-10435.
Escobedo et al. A Common PDGF Receptor Is Activated by Homodimeric A and B Forms of PDGF, *Science*, vol. 240 (1988); 1532-1534.
Claesson-Welsh et al. cDNA Cloning and Expression of a Human Platelet-Derived Growth Factor (PDGF) Receptor Specific for B-Chain-Containing PDGF Molecules, *Molecular and Cellular Biology*, vol. 8, No. 8 (1988); 3476-3486.
Johnson et al. Platelet-Derived Growth Factor: Identification of Constituent Polypeptide Chains, *Biochemical and Biophysical Research Communications*, vol. 104, No. 1 (1982); 66-74.
Hart et al. Synthesis, Phosphorylation, and Degradation of Multiple Forms of the Platelet-derived Growth Factor Receptor Studied Using a Monoclonal Antibody, *Journal of Biol. Chem.*, vol. 262, No. 22, (1987), 10780-10785.

* cited by examiner

*Primary Examiner*—Marjorie A. Moran
*Assistant Examiner*—Anna Skibinsky
(74) *Attorney, Agent, or Firm*—Needle & Rosenberg PC

(57) ABSTRACT

A DNA sequence which encodes a human type α platelet derived growth factor receptor protein which preferentially binds to the AA homodimer and AB heterodimer forms of platelet derived growth factor and also binds the BB homodimer at high affinity, is described. Substantially pure human a platelet derived growth factor receptor protein and methods for recombinantly producing human α platelet derived growth factor receptor protein are also described.

15 Claims, 14 Drawing Sheets

Figure 3. See Legend on next page

Figure 6. See Legend on next page.

COMPOSITIONS OF ALPHA PLATELET DERIVED GROWTH FACTOR RECEPTOR NUCLEIC ACID AND PROTEIN AND METHOD OF MAKING

This application is a continuation of application Ser. No. 07/915,884, filed Jul. 20, 1992 now abandoned, which is a continuation of Ser. No. 07/308,282, filed on Feb. 9, 1989, now abandoned.

FIELD OF THE INVENTION

The present invention relates to genes which encode receptor proteins for Platelet-Derived Growth Factor (PDGF), particularly to those human genes encoding receptor proteins which preferentially bind the major form of human PDGF which is found in platelets. This invention also relates to synthesis of products of such PDGF receptor genes by recombinant cells, and to the manufacture and use of certain other novel products enabled by the identification and cloning of DNAs encoding these receptors.

BACKGROUND OF THE INVENTION

Genes encoding growth factors and their receptors have been implicated in the regulation of normal cell growth and development. There is also increasing evidence that genetic alterations affecting expression of such genes can contribute to altered cell growth associated with malignancy. The normal homologues of some oncogenes code for membrane-spanning growth factor receptors with tyrosine kinase activity (J. Downward et al., ibid. 307, 521 (1984); A. Ullrich et al., ibid. 309, 418 (1984); C. J. Sherr et al., Cell 41, 665 (1985); L. Coussens et al., Nature 320, 277 (1986)). Other oncogenes appear to act in pathways of growth factor activated cell proliferation as well (J. M. Bishop, Science 235, 305 (1985); R. A. Weinberg, ibid. 230, 770 (1985); S. K. Hanks, A. M. Quinn, T. Hunter, ibid. 241, 42 (1988)). Thus, increased knowledge of growth factor regulatory systems in general is expected to provide better understanding of genes critically involved in both normal growth control and neoplasia.

Platelet-Derived Growth Factor (PDGF) is of particular importance because it is a major connective tissue cell mitogen which is thought to play a major role in normal wound healing. Further, the abnormal expression of PDGF has been implicated not only in cancers, but also in a variety of histopathologic states including arteriosclerosis, arthritis, and fibrotic diseases (R. Ross, E. W. Raine, D. F. Bowen-Pope, Cell 46, 155(1986)).

PDGF consists of a disulfide-linked dimer of two polypeptide chains, designated A and B. There is evidence for the natural occurrence of all three possible dimeric structures containing A or B chains or both (R. F. Doolittle et al., Science 221, 275 (1983); M. D. Waterfield et al., Nature 304, 35 (1983); K. C. Robbins et al., ibid. 305, 605 (1983); C.-H. Heldin et al., Nature 319, 511 (1986); P. Stroobant and M. D. Waterfield, EMBO J. 3, 2963 (1984)). The various dimeric forms of the growth factor are called "isoforms". A variety of normal and neoplastic cells appear to specifically express either the A or B chains. Nevertheless, the most significant human isoform for physiological regulatory processes is believed to be the one isolated from human platelets, namely the AB heterodimer (i.e., a dimer containing one A and one B chain; see reference A. Johnsson, C.-H. Heldin, B. Westermark, A. Wasteson, Biochem. Biophys. Res. Commun. 104, 66 (1982)).

The PDGF-A and B chains have distinguishable properties (P. Beckman et al., Science 241, 1346 (1988)). The A chain is much more efficiently secreted and exhibits lower specific mitogenic activity than the B chain. The B chain gene of PDGF has been shown to be the normal human homologue of the simian sarcoma virus-derived v-sis oncogene. Moreover, there is accumulating evidence that expression of the B chain in cell types possessing PDGF receptors can drive such cells along the pathway to malignancy. The A chain is less potent than the B chain in inducing neoplastic transformation of cultured mouse (NIH/3T3) cells.

Recent studies have suggested the existence of two subtypes of the PDGF receptor (PDGF-R), on the basis of PDGF isoform binding and competition using mouse or human fibroblasts (C.-H. Heldin et al., ibid. 7, 1387 (1988); C. E. Hart et al., Science 240, 1529 (1988)). These works are consistent with the hypothesis that there exists one receptor subtype which preferentially binds the B chain dimer, and another which efficiently binds all isoforms of the PDGF molecule. However, the results of these studies could not discriminate between two distinct possibilities with differing implications for the study and ultimate treatment of diseases involving such receptors: either these subtypes represent differently processed products of a single PDGF-R gene; or they are products of distinct genes.

Further, there have been conflicting findings concerning binding of different PDGF isoforms of the receptor produced by a previously identified human PDGF-R gene. Introduction of PDGF-R genes by expression vectors into different cell types devoid of PDGF receptors has been reported to lead either to preferential binding of PDGF-BB (R. G. K. Gronwald et al., ibid. 88, 3435 (1988); L. Claesson-Welsh et al., Mol. Cell. Biol. 8, 3476 (1988)) or, alternatively, to efficient binding by all three isoforms (J. A. Escobedo et al., ibid. 240, 1532 (1988)). The basis of this discrepancy is not known.

Thus, there has been uncertainty concerning the ability of the known PDGF receptor to respond to different PDGF isoforms, and to the main AB heterodimer form of human PDGF, in particular. Some reported differences might be explained by cell specific differences in post-translational processing of the product of the known PDGF-R gene, or by the presence of accessory proteins in certain cell types. Alternatively, the different binding properties reported in different studies might be explained by the existence of two distinct genes encoding different PDGF receptors.

In light of the complexities of PDGF ligand and receptor activities described above, and the related processes which are influenced thereby, comprising both normal wound healing and abnormal connective tissue conditions, including neoplastic growth, arteriosclerosis, arthritis, and fibrotic diseases, it is apparent that there has been a need for methods and compositions and bioassays which would provide an improved knowledge and analysis of mechanisms of connective tissue growth regulation, and, ultimately, a need for novel diagnostics and therapies based on the PDGF receptors involved therein.

In particular, the observations above, indicate a specific need for thorough characterization of the genetic basis of PDGF receptor production. Furthermore, it has been shown previously (C. R. King, M. H. Kraus, S. A. Aaronson, ibid. 229, 974 (1985); G. D. Kruh et al., ibid. 234, 1545 (1986)) that it is possible to identify and clone novel related members of the gene family encoding membrane-spanning growth factor receptors with tyrosine kinase activity, which comprises the known PDGF receptor gene and the kit and fms oncogenes, by exploiting the conserved tyrosine kinase coding region as a probe.

Accordingly, the present invention contemplates the application of methods of recombinant DNA technology to fulfill the above needs and to develop means for producing PDGF receptor proteins which appear to be the predominant effectors of the main form of human PDGF. This invention also contemplates the application of the molecular mechanisms of these receptors related to healing and pathological processes.

In particular, it is an object of the present invention to identify and isolate the coding sequence of a novel human gene related to but distinct from the known PDGF-R gene, as well as from other members of the family of tyrosine kinase genes comprising the PDGF-R, kit, and fms genes. Further, it is an object of this invention to develop the molecular tools needed to establish the relative roles of the novel and known forms of PDGF receptor in physiological processes involving PDGF.

SUMMARY OF THE INVENTION

The present invention relates to a development of recombinant DNA technology, which includes production of novel PDGF receptor (PDGF-R) proteins, free of other peptide factors. Novel DNA segments, RNAs, and bioassay methods are also included.

The present invention in particular relates, in part, to DNA segments which encode messenger RNAs (mRNAs) and proteins having structural and/or functional characteristics of a new human receptor within the subfamily of membrane-spanning tyrosine kinase receptor genes comprising the following known receptor genes: the PDGF-R gene; colony stimulating factor one receptor (CSF1-R) gene (also known as a cellular form of the fms oncogene, c-fms); and a cellular form of the kit oncogene (c-kit) (see reference (C. J. Sherr et al., Cell 41, 665 (1985); L. Coussens et al., Nature 320, 277 (1986); Y. Yarden et al., Nature 323, 226 (1986); P. Besmer et al., ibid. 320, 415 (1986); Y. Yarden et al., EMBO J. 6, 3341 (1987)) for background).

More specifically, this invention includes DNA segments containing a genomic DNA sequence or a DNA sequence complementary to the mRNA transcribed from said genomic DNA (i.e., a "cDNA"), with a predicted protein product similar in structure to other receptors of this growth factor receptor subfamily. Among these receptors, the predicted novel gene product exhibits closest sequence homology to the known PDGF receptor.

Further, this novel product encoded by DNAs of this invention is coexpressed with the known PDGF receptor gene product in a variety of normal cell types. This protein product can bind to and be functionally activated by PDGF. However, the activities of different PDGF isoforms functionally distinguish the new product, herein designated the type α human PDGF receptor, from that of previously identified genes encoding receptors that can bind PDGF, including the known receptor previously termed the PDGF receptor and herein designated as the type β PDGF receptor. Moreover, considerable evidence disclosed herein indicates that this novel gene product, the type α PDGF receptor, is the main effector of activity for the most abundant form of PDGF in the human body.

In the practice of one embodiment of this invention, the DNA segments are capable of being expressed in suitable host cells, thereby producing the novel PDGF receptor proteins. This invention also relates to mRNAs produced as the result of transcription of the sense strands of the DNA segments of this invention. The invention further comprises novel bioassay methods for determining levels of expression in human cells of the mRNAs and proteins produced from the genes related to DNA segments of the invention.

In a principal embodiment, the present invention comprises DNA segments encoding novel PDGF receptors, as exemplified by the following: a clone of genomic normal human thymus DNA, herein designated as the T11 genomic clone; human cDNA clones of cell mRNAs containing sequences contained in T11, designated HF1, HB6, EF17 and TR4; and related DNA segments which can be detected by hybridization to any of the above human DNA segments, which related segments encode receptor genes, wherein said genes do not include previously known PDGF-related receptor genes.

The human gene related to clone T11 are referred to hereinafter as "the T11 gene" and use of the term "T11" as an adjective is intended to include any of the above DNA segments of this invention, absent a specific reference to "the T11 genomic clone".

In another embodiment, this invention relates to a recombinant DNA molecule comprising a vector and a DNA of the present invention. These recombinant molecules are exemplified by molecules comprising genomic or cDNA clones related to the T11 gene and any of the following vector DNAs: a bacteriophage λ cloning vector; or an expression vector capable of expressing inserted DNAs in mammalian cells.

In still another embodiment, the invention comprises a cell, preferably a mammalian cell, transformed with a DNA of the invention. Further, the invention comprises cells, including yeast cells and bacterial cells such as those of E. coli and B. subtilis, transformed with DNAs of the invention. According to another embodiment of the invention, the transforming DNA is capable of being expressed in the cell, thereby increasing the amount of PDGF-R protein encoded by this DNA, in the cell.

Still further, the invention comprises novel PDGF-R proteins made by expression of a DNA of the invention, or by translation of an RNA of the invention. These receptors can be used for functional studies, and can be purified for additional biochemical and functional analyses, such as qualitative and quantitative receptor binding assays.

In particular, these type α PDGF receptors may be used for the development of therapies for conditions involving abnormal processes involving PDGF and its receptors, by testing receptor binding and activation activities of potential analogs (either antagonists or agonists) of the various PDGF isoforms, including the main form of human PDGF.

According to this aspect of the invention, the novel PDGF-R proteins can be protein products of "unmodified" DNAs and mRNAs of the invention, or they can be modified or genetically engineered protein products. As a result of engineered mutations in the DNA sequences, modified PDGF-R proteins have one or more differences in amino acid sequence from the corresponding naturally occurring "wild-type" proteins. These differences may impart functional differences to the modified gene products such as improvements in their manufacturability or suitability for use in bioassays.

This invention also relates to novel bioassay methods for detecting the expression of genes related to DNAs of the invention. According to one such embodiment, DNAs of this invention, particularly the most preferred DNAs, may be used as probes to determine specific levels of mRNAs related to type α PDGF receptors, without interference from mRNAs of known PDGF receptor genes. Such bioassays may be useful, for example, for identification of various classes of tumor cells or of genetic defects in administration of polypeptides that are well known in the art and can be adapted readily for administration of the present antibodies without undue experimentation.

These antibodies, and active fragments thereof, can be used, for example, for specific detection or purification of either the novel type α PDGF receptor, or, alternatively, of the known type β PDGF receptor. Such antibodies could also be used in various methods known in the art for targeting drugs to tissues with high levels of PDGF receptors, for example, in the treatment of appropriate tumors with conjugates of such antibodies and cell killing agents.

BRIEF DESCRIPTION OF THE FIGURES

FIG. 3 contains the nucleotide sequence (SEQ ID NO: 2) and deduced amino acid sequence (SEQ ID NO: 1) of the novel type α PDGF receptor encoded by the $T_4$ cDNA. Nucleotides are numbered at the left. The predicted amino acid sequence of the long open reading frame is shown above the nucleotide sequence. Amino acids are numbered over the amino acids: starting at the putative initiation codon. The potential N-terminal signal sequence is underlined. Potential sites of N-linked glycosylation are overlined, and cystine residues are boxed. The putative single transmembrane region is indicated by a shaded bar. The potential ATP binding site in the kinase domain is indicated by circles over Gly at residue 600, 602 and 605 and Lys at residues 627. The putative tyrosine autophosphorylation site at residue 849 is indicated by the $T_4$ cDNA. The regions of the T11 genomic sequence defined by exons a, b and c are underlined. The AATAAA box close the polyadenylated 3' end of the cDNA is underlined as well.

DESCRIPTION OF SPECIFIC EMBODIMENTS

The DNAs of this invention are exemplified by DNAs referred to herein as: the T11 genomic clone; and clones HF1, HB6, EF17 and TR4, comprising human cDNA clones of cell mRNAs containing sequences included in the T11 genomic clone.

The T11 genomic clone and the TR4 cDNA clone are preferred DNAs of this invention. A clone designated pT11-HP (a HindIII-PstI 0.95-kbp fragment of genomic clone T11) and a particular restriction fragment from a T11cDNA (3.5-kbp BamHI fragment of TR4, including the whole coding region) are most preferred DNAs of this invention.

Figure 2:
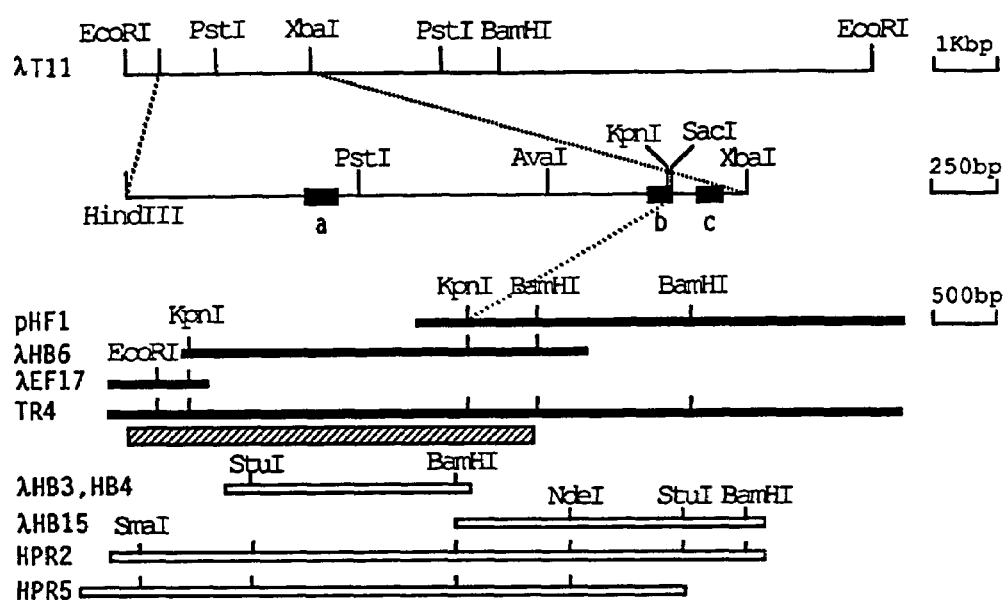
FIG. 2 presents the restriction map of the novel v-fms-related gene (T11) and related human PDGF receptor cDNA clones. The restriction map shows [lambda]T11 genomic clones (solid lines); T11 cDNA clones (solid bars); and PDGF-R cDNA clones (open bars). Coding regions within 3 fragments, as determined by nucleotide sequencing analysis, are indicated by black boxes labeled a, b, and c.

The restriction enzyme digestion maps of cDNA clones HF1, HB6, EF17 and TR4, and their mapping relationships to genomic clone T11, are displayed in FIG. 2. The sense strand DNA nucleotide sequence, and the predicted primary protein sequence encoded, are shown in FIG. 3 for the TR4 cDNA clone, the largest cDNA clone related to the T11 gene.

Figure 1:
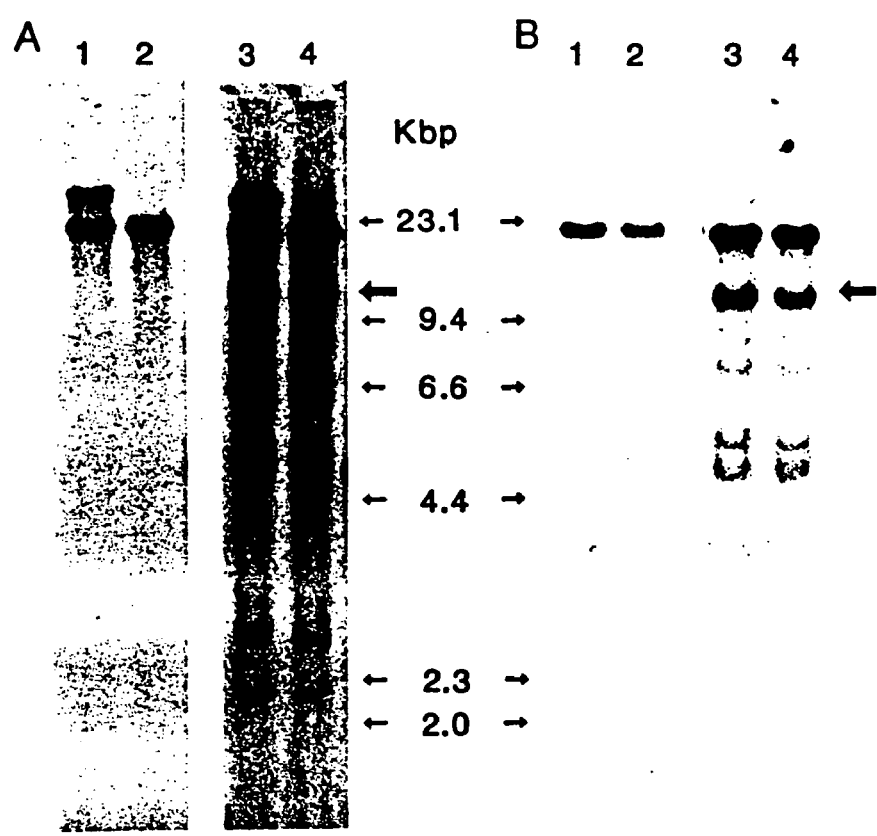
FIG. 1 illustrates detection of gene fragments related to the oncogene v-fms and to the known mouse PDGF receptor in human placenta and thymus DNAs by Southern blot hybridization analyses Hybridization of a v-Fms probe (A) or a mouse PDGF receptor probe (B) to human placenta (lane 1 and 3) or thymus (lane 2 and 4) DNAs under stringent (50% formamide; lane 1 and 2) or relaxed (30% formamide; lane 3 and 4) hybridization conditions. Arrows indicate the 12-Kbp EchoRI fragment detected under relaxed conditions by both v-Fms and mouse PDGF-R probes.

As described in the Experimental Section, the T11 genomic clone comprises a clone of genomic fragment of normal human thymus DNA containing a 12-kbp sequence bounded by recognition sites for the restriction enzyme EcoRI, which fragment hybridized more strongly in analyses by blot hybridization than other fragments with DNA probes derived from the tyrosine-kinase domains of both the viral oncogene v-fms and the mouse cellular PDGF-R gene (see FIG. 1). The T11 genomic clone contains most of the blocks of sequences found in the mRNA product of the T11 gene (i.e., the exons), in addition to intervening gene sequences not found in the mRNA (i.e., introns).

Other DNAs of this invention include the recombinant molecules comprising T11-related genomic or cDNA clones of this invention and any of the following vector DNAs: a bacteriophage λ cloning vector (exemplified by λEMBL4 or λgt11); or a mammalian expression vector (such as the pSV2 gpt vector into which the simian sarcoma virus promoter was engineered) capable of expressing inserted DNAs in mammalian (e.g., COS-1) cells.

Genomic clone T11 DNA was isolated, by standard gene cloning methods well known in the art, from a genomic library constructed from EcoRI-digested normal human thymus DNA which was size-selected by sucrose gradients and cloned into the λEMBL-4 vector system. The λT11 clone was identified on the basis of hybridization with both v-fms and mouse PDGF-R probes only under relaxed but not stringent hybridization conditions. Further details of the cloning strategy and probes are provided below and in the following Experimental Section.

A plasmid containing the HF1 cDNA clone, designated pHF1, was isolated by standard, well known methods, from a normal human fibroblast cDNA library in the Okayama-Berg expression vector under stringent conditions using the 0.9-kbp HindIII-PstI fragment of λT11 which is a most preferred DNA of this invention. It contains a 3.9-kbp cDNA insert which hybridized to a 6.4-kb RNA transcript in normal human fibroblasts and contains a polyadenylation signal followed by a poly(A) tail at its 3' end. It also contains the coding sequence within the λT11 DNA and 170 nucleotides related to CSF1-R and PDGF-R tyrosine kinase domains upstream of exon (a). Plasmid HF1 was deposited at the American Type Culture Collection and has the following accession number: 75058.

The cDNA clone λHB6 was isolated by standard methods using the 0.4-kbp 5' end of clone HF1 to screen a human infant brain cDNA library in the λgt11 vector.

Another cDNA clone, λEF17, isolated by screening a human embryo fibroblast (M426 cell line) cDNA library, prepared by random priming of DNA synthesis on mRNA template and cloning in the λgt11 vector, with a 0.2-kbp 5' fragment of λHB6 as a probe. A possible ATG initiation codon was identified within EF17.

The three overlapping clones (pHF1, AHB6 and λEF17) contain the entire coding region in addition to 138-bp 5' and ~3-kbp of 3' untranslated sequences (FIG. 2).

Figure 4:
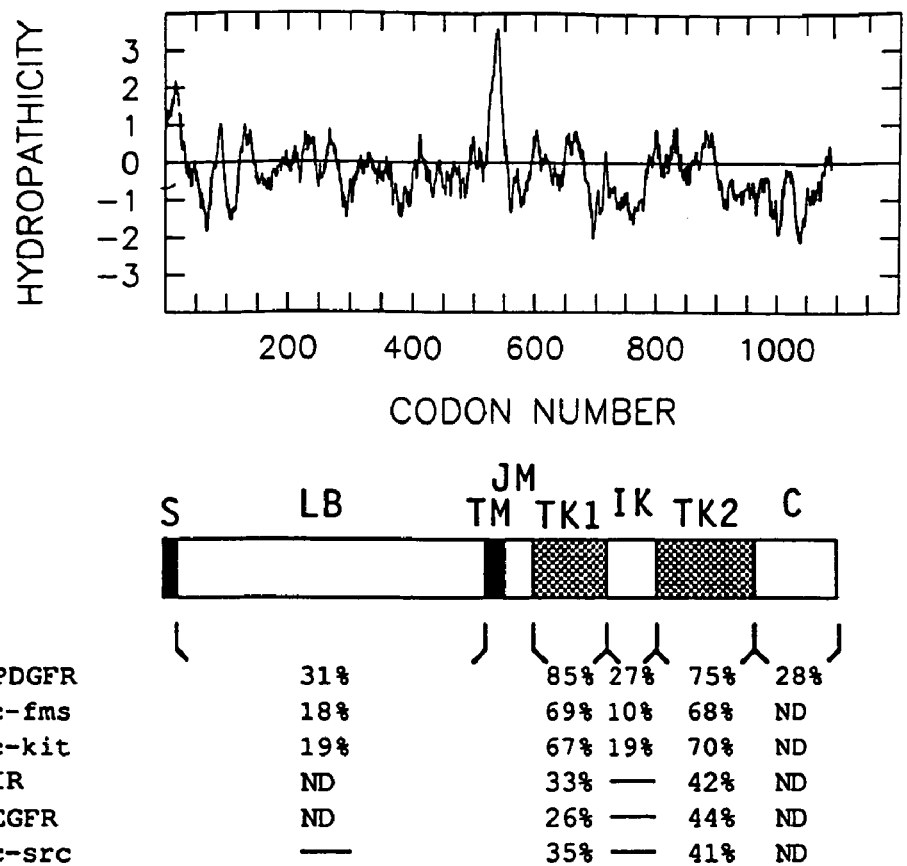
FIG. 4 depicts results of hydropathicity analysis of human type α PDGF receptor and homologies of deduced amino acid sequences in comparison with the known type β PDGF receptor and other receptors. A schematic diagram of the predicted protein domains shows the signal sequence (S; black box), ligand binding domain (LB), transmembrane domain (TM; second black box), juxtramembrane domain (JM), tyrosine kinase domains (TK1, TK2; hatched boxes), inter-kinase domain (IK) and carboxyl terminus (C). The hydropathicity profile was calculated by the method of Kyte and Doolittle. The homology percentage is shown refer to identical amino acids within each respective domain. Abbreviations: IR, insulin receptor; EGF-R, epidermal growth factor receptor; ND, not determined.

The cDNA clone TR4 was obtained using a 5' 0.2-kbp subfragment of λEF17 to screen a M426 human embryo fibroblast cDNA library in a "phagemid" (phage and plasmid hybrid) vector (Subject of the U.S. patent application entitled "Efficient Directional Cloning System", to be filed February, 1989). The 6.4-kbp TR4 cDNA clone includes an open reading frame beginning with a possible ATG initiation codon at nucleotide position 139 and extended to a TAA termination codon at position 3406 (see FIG. 3). Moreover, the first 23 amino acid stretch displayed properties of a cleavable hydrophobic signal peptide (FIGS. 3 & 4). The open reading frame was followed by ~3-kbp of untranslated sequences and a polyadenylation signal (AATAAA) located 25 nucleotides upstream from the poly(A) sequence at the 3' end of the cDNA.

cDNA expression plasmids were constructed using standard cloning methods well known in the art, by introducing the T11-related cDNA encompassing nucleotides 1 to 3454 (FIG. 3) into the pSV2 gpt vector into which the simian sarcoma virus long-terminal-repeat (LTR) had been engineered as the promoter, as previously described in detail (C. R. King, N. A. Giese, K. C. Robbins, S. A. Aaronson, Proc. Natl. Acad. Sci. USA 82, 5295 (1985)).

DNAs and sense strand RNAs of this invention can be employed, in conjunction with protein production methods known in the art, to produce cells expressing functional type α PDGF-R protein from the novel gene in the absence of other PDGF receptors. These novel receptors can be used for functional studies in cells, such as qualitative and quantitative receptor binding assays.

Accordingly, one embodiment of this aspect of this invention comprises a cell, preferably a mammalian cell, transformed with a DNA of the invention, wherein the transforming DNA is capable of being expressed. Mammalian cells (COS-1) transformed with the pSV2 gpt vector carrying a T11-related cDNA were prepared according to well-known methods and were shown to express T11 gene products as 185 kd and 160 kd species (FIG. 7B). These products were capable of binding human PDGF isolated from platelet, as illustrated in the Experimental Section below (see, FIG. 8).

Additional work in the Experimental Section demonstrates further that DNAs of this invention can be used to reconstitute type α PDGF receptor gene function in other cells free of PDGF receptors, and that each receptor type, α or β, efficiently mediates major known PDGF activities including mitogenic signal transduction, chemotaxis and stimulation of phosphoinositide turnover. Moreover, these studies further establish the type α PDGF receptor as the principal receptor for the main form of human PDGF which is derived from platelets.

Thus, by so using the DNAs of the invention in gene expression methods, especially the preferred TR4 cDNA clone listed herein, those skilled in the art, without undue experimentation, can construct cell systems which fall within the scope of this invention, for determining the mechanisms of PDGF regulatory processes, as well as for production of large amounts of the novel PDGF receptor protein.

Figure 6:
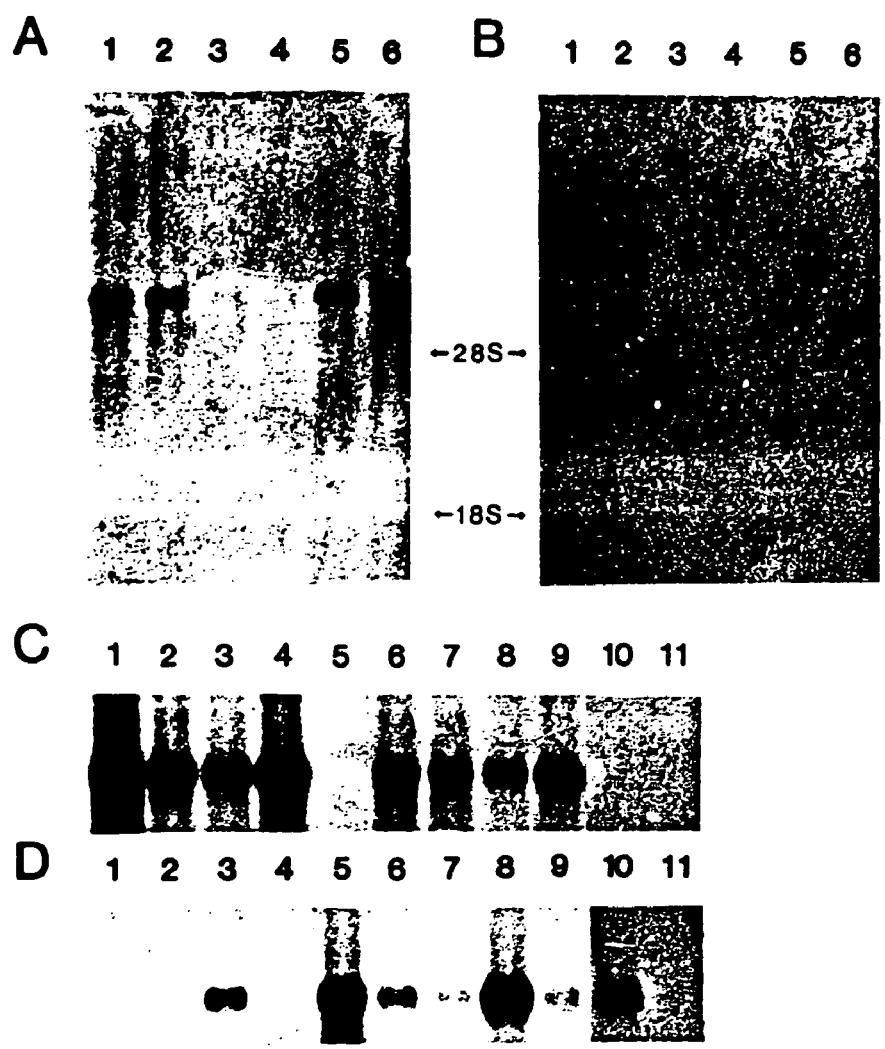
FIG. 6 is a comparison of mRNA species produced from the type α and β PDGF receptor genes. The same filter was first hybridized with the probe from pT11-HP (0.95-Kbp HindIII-PstI genomic fragment) (A) and then rehybridized with a PDGF-R cDNA probe (B). A different filter was first hybridized with T11 cDNA (3.5-Kbp BamHI fragment of TR4 including the whole coding region) (C) and then rehybridized with PDGF-R cDNA (3.8-KBP NdeI fragment of HPR2) (D). A and B contain poly (A)+ RNAs (5 µg per lane) extracted from human smooth muscle (lane 1), heart (lane 2), liver (lane 3), spleen (lane 4) or embryo (lanes 5 and 6). C and D contained total RNA (20 µg per lane) extracted from G402 leiomyoblastoma cells (lane 1), SK-LMS-1 leiomyosarcoma cells (lane 2), A1186 or A204 rhabdomyosarcoma cells (lanes 3 and 4), 8387 fibrosarcoma cells (lane 5), astrocytoma tissues (lanes 6 and 7), A1690 astrocytoma cells (lane 8), A1207 or A172 glioblastoma cells (lanes 9 and 10) or A875 melanoma cells (lane 11). Migration of 28S and 18S ribosomal RNA (markers) are as indicated.

This invention further comprises novel bioassay methods for detecting the expression of genes related to DNAs of the invention. According to one such embodiment, DNAs of this invention may be used as probes to determine levels of related mRNAs. This embodiment is exemplified by the comparison of mRNA species of the T11 and known PDGF-R genes in normal and tumor cells (FIG. 6). Total or polyadenylated RNA was separated by denaturing gel electrophoresis in formaldehyde (H. D. Lehrach, D. Diamond, J. M. Wozney, H. Boedtker, Biochemistry 16, 4743 (1977)), transferred to nitrocellulose, and hybridized under stringent conditions with $^{32}$P-labeled probes. The probes were prepared from any of the following DNAs of this invention: clone pT11-HP (0.95-kbp HindIII-PstI fragment of genomic clone T11); or from T11 cDNA (3.5-kbp BamHI fragment of TR4, including the whole coding region).

Therefore, by employing the DNAs and RNAs of the invention in known hybridization methods, especially the most preferred DNAs listed herein, those skilled in the art, without undue experimentation, can measure levels of expression of type α PDGF-R gene without interference from mRNA of type β PDGF-R gene or other related oncogenes.

This invention also comprises novel antibodies made against a peptide encoded by a DNA segment of the invention or by other related DNAs. This embodiment of the invention is exemplified by rabbit antisera containing antibodies which specifically bind to type α PDGF-R protein or, in the alternative, to the known PDGF-R protein, herein designated type β.

Such type specific antisera were raised to synthetic peptides representing 15 amino acid sequences from the carboxyl-terminal regions of their respective PDGF-R proteins (residues 959-973 of the type α sequence displayed in FIG. 3, and corresponding residues 967-981 of the known type β sequence, as predicted by the respective cDNA sequences). These peptides were selected to meet the following criteria: lack of sequence relatedness between the two PDGF-R types (less than 50% sequence homology); relative hydrophilicity; and carboxyl-terminal location which is known to be associated with a higher likelihood of producing antibodies reactive with native proteins.

Antisera to peptides were prepared by chemically synthesizing the peptides, conjugating them to carrier (thyroglobulin), and injecting the conjugated peptides into rabbits with complete Freund's adjuvant, according to standard methods of peptide immunization.

Figure 7:
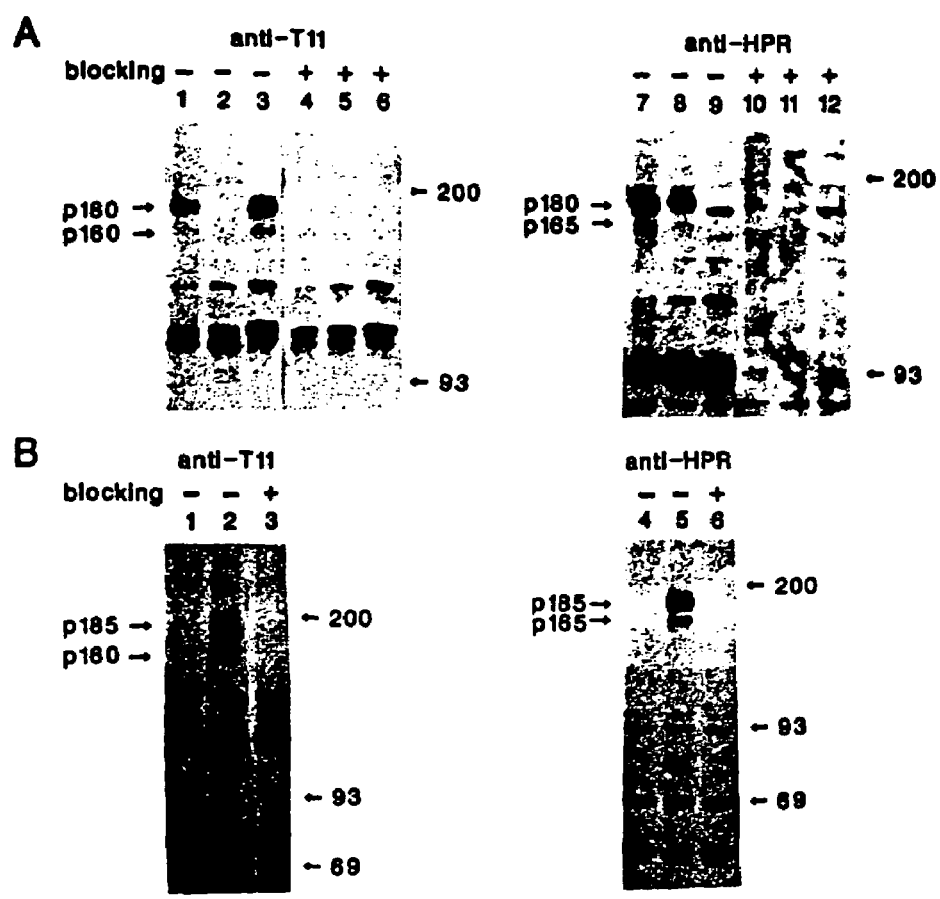
FIG. 7 demonstrates specific detection of type α or type β proteins with peptide antisera in human cell lines or in monkey (COS-1) cells transformed with a $T_4$ cDNA in an expression vector. Detection of T11 and PDGF-R proteins with peptide antisera is shown in human cells lines (A) and COS-1 cell transfectants (B). (A) M426 human embryo fibroblast (lanes 1, 4, 7 and 10), 8387 fibrosarcoma cells (lanes 2, 5, 8 and 11), A204 rhabdomyosarcoma cells (lanes 3, 6, 9 and 12), (B) COS-1 cells (lanes 1 and 4), COS-1 cells transfected with vectors carrying T11 cDNA (lanes 2 and 3) or PDGF-R cDNA (lanes 5 and 6).

These antibodies can be used for detection or purification of the protein products. Thus, FIG. 7 shows the use in Western blot experiments of two different rabbit antibodies [anti-T11 (PDGF-R type α) and anti-HPR (PDGF-R type β)] raised against the corresponding type-specific peptides. As is evident from the figure, the appropriate PDGF-R types are specifically detected in various cells by antisera from rabbits immunized with synthetic peptides.

EXPERIMENTAL SECTION

This section describes experimental work leading to the identification and cloning of a genomic sequence and cDNAs of a novel receptor-like gene of the PDGF receptor/CSF-1 receptor subfamily. The gene gives rise to a 6.4-kb RNA transcript that is coexpressed in normal human tissues with the known 5.3-kb PDGF receptor mRNA. The new PDGF receptor gene was localized to chromosome 4 at location 4q 11-12, consistent with the clustering of other genes of this receptor subfamily on ancestrally related chromosomes 4 and 5.

That the cloned cDNA is functional is demonstrated by the observation that introduction (by transfection using a viral vector) of a cDNA of the novel gene into COS-1 cells leads to expression of proteins which are specifically detected with anti-serum directed against a predicted peptide. Transfected but not control COS-1 cells demonstrate specific binding of $^{125}$I-human PDGF, which is efficiently competed by all three PDGF isoforms, including the main AB form found in human platelets. In contrast, expression of the known PDGF receptor cDNA in COS-1 cells leads to PDGF binding with a distinct pattern of competition by the same PDGF isoforms characterized by a marked preference for PDGF form BB.

Further evidence that the new receptor gene encodes a distinct PDGF receptor derives from examination of human cells, originally free of PDGF receptors, in which PDGF-receptor activities are reconstituted by either type α or type β receptors introduced by transfection with vectors bearing the respective cDNAs. Cells with the type α receptors are significantly more responsive to PDGF-AB in all of the following PDGF-mediated cellular activities: tyrosine phosphorylation of the receptor gene product; stimulation of DNA synthesis and consequent cell proliferation; chemotaxis; phosphoinositide breakdown; and cytosolic calcium mobilization ([$Ca^{2+}$]i).

Thus, while each type of reconstituted PDGF-R gene product independently elicits similar biochemical as well as biological responses to PDGF-BB, the type α PDGF-R is the preferred receptor for PDGF-AB, the principal isoform of human PDGF which is found in platelets. Accordingly, it follows that abnormalities in the structure or expression of the type α PDGF receptor could have profound pathological effects for which the present invention provides means of diagnosis and therapy.

MATERIALS AND METHODS

Detection of v-fms and PDGF receptor-related gene fragments in human placenta and thymus DNAS. Genomic DNA (20 μg) was digested with EcoRI, separated by electrophoresis in 0.8% agarose gels, and transferred to nitrocellulose paper (E. M. Southern, J. Med. Biol. 98, 503(1975)). Hybridization to $^{32}$P-labeled probes (P. W. J. Rigby, M. Dieckerman, C. Rhodes, P. Berg ibid. 113, 237(1977)) was conducted in a solution of 50% or 30% formamide, 0.75 M NaCl, and 0.075 M sodium citrate, at 42° C. (G. M. Wahl, M. Stern, G. R. Stark, Proc. Natl. Acad. Sci. USA 76, 3683 (1979)). After hybridization, the blots were washed in 2×SSC (0.3 M NaCl; 0.03 M sodium citrate) at room temperature, and then in 0.1× or 0.6×SSC at 50° C. (stringent or relaxed condition, respectively). The v-fms probe was a 0.44-kbp XhoI-BglII fragment encompassing nucleotides 3891 to 4419 of the v-fms oncogene (A. Hampe, M. Gobet, C. J. Sherr, F. Galibert, ibid. 81, 85 (1984)). The mouse PDGF receptor probe was a 0.5-kbp SinI-PvuI fragment encompassing nucleotide 2490 to 2995 of its cDNA (Y. Yarden et al. Nature 323, 226 (1986)).

Molecular cloning of the λT11 genomic fragment as well as cDNAs of T11 and PDGF-R genes. Libraries from which specific cDNA clones (in parentheses) were isolated included: human fibroblast mRNAs in the Okayama-Berg vector (pHF); human infant brain mRNAs in λgt11 (λHB); human embryonic fibroblast random primed mRNAs in λgt11 (λEF); and human embryonic fibroblast mRNAs in the directional cloning phagemid (TR4 or HPR). Restriction sites were determined by electrophoretic analysis of the products of single and double digestions. Regions of λT11 homologous to the v-fms or mouse PDGF receptor probes were identified by hybridization as described in FIG. 1. Three restriction fragments (0.95-kbp HindIII-PstI, 0.5-kbp AvaI-SacI, and 0.35-kbp KpnI-XbaI) including regions homologous to the v-fms and mouse PDGF receptor probes were subcloned into plasmids and sequenced by the dideoxy chain termination method (F. Sanger, S. Nicklen, A. R. Coulson, ibid. 74, 5463 (1977)).

Chromosome mapping of the T11 gene. The probe was labeled with all four $^3$H-nucleotides (New England Nuclear, Boston, Mass.) using a modified nick translation kit (Amersham, Arlington Heights, Ill.) to a specific activity of $2.5 \times 10^7$ cpm/µg DNA. In situ hybridization with human metaphases and prometaphases from methotrexate-synchronized peripheral lymphocyte cultures was carried out as previously described (M. E. Harper and G. F. Saunders, Chromosoma (Berl.) 83, 431 (1981); N. C. Popescu et al., Cytogenet. Cell Genet. 39, 73 (1985)).

Comparison of mRNA species by Northern blot hybridization. Total or polyadenylated RNA was separated by denaturing gel electrophoresis in formaldehyde (H. D. Lehrach, D. Diamond, J. M. Wozney, H. Boedtker, Biochemistry 16, 4743 (1977)), transferred to nitrocellulose, and hybridized under stringent conditions (50% formamide, 0.075M NaCl, 0.75M sodium citrate, at 42° C.) with $^{32}$P-labeled probes.

Detection of T11 and PDGF-R proteins with peptide antisera. Anti-T11 and anti-PDGF-R sera were obtained following immunization of rabbits with 15 amino acid peptides from the corresponding carboxyl-terminal regions of the predicted receptors. These peptide sequences were less than 50% homologous. cDNA expression plasmids were constructed by introducing the T11 cDNA encompassing nucleotides 1 to 3454 (FIG. 3) or the PDGF-R cDNA encompassing nucleotides 1 to 3939 into the pSV2 gpt vector into which the simian sarcoma virus LTR had been engineered as the promoter (C. R. King, N. A. Giese, K. C. Robbins, S. A. Aaronson, Proc. Natl. Acad. Sci. USA 82, 5295 (1985)). About $10^6$ COS-1 cells in 10 cm petri dishes were incubated in Dulbecco's modified Eagle's medium (DMEM) supplemented with 10% fetal calf serum 24 hr prior to transfection. DNA transfection was performed by the calcium phosphate precipitation method (M. Wigler et al., Cell 11, 223 (1977)) 48 hours prior to analysis. Cultures were lysed with staph-A buffer (10 mM sodium phosphate pH7.5, 100 mM NaCl, 1% TRITON X-100, (polyethylene glycol p-isocytlphennyl ether) 0.1% SDS, 0.5% deoxycholate, 0.1% aprotinin, 1 mM PMSF, and 1 mM sodium orthovanadate) and clarified by centrifugation at 10,000×g for 30 min. Proteins (100 µg per lane) were resolved by electrophoresis in 7% SDS-polyacrylamide gels, transferred to nitrocellulose filters and probed by immunoblot analysis (with or without peptide blocking) using $^{125}$I-Protein A (H. Towbin, T. Staehlin, J. Gordon, Proc. Natl. Acad. Sci. USA 76, 4350 (1979)).

Binding of $^{125}$I-labeled human PDGF to receptors on cells. COS-1 cells were plated in 12-well plates and transfected 48 hours before assay as described in FIG. 7. Human PDGF was labeled with $^{125}$I by the chloramine-T method T specific activities of $3.7 \times 10^4$ cpm/ng (W. M. Hunter and F. C. Greenwood, Nature 194, 495 (1962)). The binding of $^{125}$I-labeled PDGF isolated from human platelets (E. W. Raines and R. Ross, J. Biol. Chem. 257, 5154 (1982)) in the absence or presence of a 50-100 fold excess of unlabeled human PDGF (AB) (Collaborative Research), recombinant PDGF-BB (AmGen) or recombinant PDGF-AA (P. Beckman et al., Science 241, 1346 (1988)), was carried out at 4° C. for 2 hrs. Unbound $^{125}$I-PDGF was removed by four successive washes with binding buffer (DMEM containing 1 mg per ml bovine serum albumin). The cells were then lysed in solubilizing buffer (1% TRITON X-100, 20 mM Hepes pH 7.4, 10% [v/v] glycerol), and radioactivity measured with a τ counter.

Tyrosine autophosphorylation of type α and type β PDGF-R gene products. After incubation with PDGF for 5 min at 37° C., cell lysates were immunoprecipitated with anti-peptide antisera. Total cell lysates or immunoprecipitates were analyzed by immunoblotting with antibodies to the receptors connective tissue growth and/or the healing response.

This invention further comprises novel antibodies made against a peptide encoded by a DNA segment of the invention or by a related DNA. In this embodiment of the invention, the antibodies are monoclonal or polyclonal in origin, and are generated using PDGF receptor-related polypeptides from natural, recombinant or synthetic chemistry sources. These antibodies specifically bind to a PDGF-R protein which includes the sequence of such polypeptide. Preferably, these antibodies bind only to type α PDGF receptor proteins or, alternatively, only to type β PDGF receptor proteins. Also, preferred antibodies of this invention bind to a PDGF receptor protein when that protein is in its native (biologically active) conformation.

Fragments of antibodies of this invention, such as Fab or F(ab)' fragments, which retain antigen binding activity and can be prepared by methods well known in the art, also fall within the scope of the present invention. Further, this invention comprises pharmaceutical compositions of the antibodies of this invention, or active fragments thereof, which can be prepared using materials and methods for preparing pharmaceutical compositions for or to phosphotyrosine (anti-P-Tyr) (J. J. Wang, Mol. Cell. Biol. 5, 3640 (1985)). The anti-phosphotyrosine antibodies were preincubated with 10 mM phosphotyrosine for blocking.

RESULTS

Detection of a novel human PDGF-R/CSF1-R-related gene. In order to explore novel sequences related to known growth factor receptor genes of the PDGF-R/CSF1-R family, high molecular weight DNAs prepared from human placenta and thymus were digested with EcoRI and analyzed by blot hybridization with DNA probes derived from the tyrosine-kinase domains of v-fms and the mouse PDGF-R gene (FIG. 1). Under stringent conditions, the v-fms probe detected EcoRI restriction fragments of 27-kbp and/or 20-kbp, due to the previously reported restriction polymorphism at this locus (D. Q. Xu, S. Guilhot, F. Galibert, Proc. Natl. Acad. Sci. USA 82, 2862 (1985)). Under less stringent conditions, several additional fragments of 12-, 6.8-, 5-, 2.7-, 2.2-kbp, which hybridized to the v-fms probe, were observed. The corresponding region of the mouse PDGF-R cDNA hybridized with a single 21-kbp fragment under stringent conditions (FIG. 1).

At lower stringency, the same probe detected several additional fragments, some of which had sizes similar to those of the v-fms-related fragments described above. Among these, the 12-kbp EcoRI fragment hybridized more strongly than the other fragments with both probes. Moreover, some of the smaller bands corresponded to restriction fragments reported for human c-kit (P. Besmer et al., ibid. 320, 415 (1986); Y. Yarden et al., EMBO J. 6, 3341 (1987)). Thus, it was decided to clone the 12-kbp EcoRI DNA fragment and characterize it more fully.

Using the λEMBL-4 vector system, a genomic library size-selected by sucrose gradients was constructed from EcoRI-digested normal human thymus DNA. FIG. 2 shows the restriction map of λT11 containing a 12-kbp EcoRI insert, which hybridized with both v-fms and mouse PDGF-R probes only under relaxed but not stringent hybridization conditions. Regions homologous to v-fms/PDGF-R tyrosine kinase domains were localized by hybridization to restriction endonuclease digests of λT11 DNA.

Three plasmid subclones containing sequences hybridizing to the 0.95-kbp HindIII-PstI, 0.5-kbp AvaI-SacI, and 0.35-kbp KpnI-XbaI fragments of λT11 were subjected to nucleotide sequence analysis. Their discrete open reading frames (FIG. 3) showed relatedness to both human c-fms and mouse PDGF-R genes, but were readily distinguished from each of these genes (C. J. Sherr et al., Cell 41, 665 (1985); L. Coussens et al., Nature 320, 277 (1986); Y. Yarden et al., Nature 323, 226 (1986)) as well as from c-kit (P. Besmer et al., ibid. 320, 415 (1986); Y. Yarden et al., EMBO J. 6, 3341 (1987)). The three putative coding regions were each flanked by the AG and GT dinucleotides that border the exons of eukaryotic genes (R. Breathnad and P. Chambon, Annu. Rev. Biochem. 50, 349 (1981)).

To assess whether the T11 sequence was transcribed, Northern blot analyses of a variety of cells were performed using a clone of the 0.95-kbp HindIII-PstI fragment (pT11-HP) which contained exon (a) (FIG. 2) and lacked human repetitive sequences. Under stringent conditions, a single 6.4-kb RNA transcript was detected in poly(A)+ RNA prepared from normal human fibroblasts (data not shown). This transcript differed in size from previously reported transcripts for the PDGF-R (Y. Yarden et al., Nature 323, 226 (1986)), c-fms (3) or c-kit genes (P. Besmer et al., ibid. 320, 415 (1986); Y. Yarden et al., EMBO J. 6, 3341 (1987)). All of these findings indicated that the T11 sequence represented a gene distinct from known members of this subfamily of tyrosine kinase receptors.

cDNA cloning of the novel gene. A normal human fibroblast cDNA library in the Okayama-Berg expression vector was initially screened under stringent conditions using the pT11-HP clone of the 0.9-kbp HindIII-PstI fragment of λT11. One strongly hybridizing clone containing a 3.9-kbp cDNA insert was isolated (FIG. 2). This clone, designated pHF1, hybridized to a 6.4-kb transcript in normal human fibroblasts and contained a polyadenylation signal followed by a poly(A) tail at its 3' end. This clone is shown in FIG. 3 starting with nucleotide 2568 and continuing through the end of the full cDNA sequence of FIG. 3. It also contained the coding sequence within the λTa11 DNA and 170 nucleotides related to CSF1-R-PDGF-R tyrosine kinase domains upstream of exon (a).

The 0.4-kbp 5' end of pHF1 was used to search for overlapping cDNA clones in a human infant brain library. Under stringent conditions, a number of positive clones with similar restriction maps were isolated (data not shown). The longest, λHB6, (FIG. 2) was subjected to sequence analysis. A possible ATG initiation codon was identified within another clone, λEF17, isolated by screening a M426 human embryo fibroblast cDNA library in the λgt11 vector with a 0.2-kbp 5' fragment of λHB6 as a probe. The three overlapping clones (pHF1, AHB6 and λEF17) contained the entire coding region in addition to 138-bp 5' and 3-kbp of 3' untranslated sequences (FIG. 2).

Two clones, λHB3 and λHB4, that gave weaker signals in plaque hybridization during screening of the human infant brain library were also sequenced. These showed close similarity to the sequence of the mouse PDGF-R cDNA (Y. Yarden et al., Nature 323, 226 (1986)). Moreover, when the 2.0-kbp insert of λHB4 was hybridized to normal human fibroblast RNA, it detected a transcript of 5.3-kb, consistent with that of the PDGF-R (Y. Yarden et al., Nature 323, 226 (1986)).

No clones containing sequences further upstream from the 5' end of λHB4 could be obtained by screening the human infant brain cDNA library in λgt11. This was accomplished by utilizing a M426 human embryo fibroblast cDNA library in a new phagemid vector constructed as described elsewhere (Subject of the U.S. patent application entitled "Efficient Directional Cloning System", to be filed February, 1989). By screening this library with a 0.3-kbp 5' subfragment of λHB3, two overlapping clones, HPR2 and HPR5, were obtained. These contained between them the entire known human PDGF-R coding sequence, its complete 3' untranslated region, and 360 nucleotides of its 5' untranslated region (FIG. 2). A 6.4-kbp cDNA clone (TR4) of the novel related gene was also obtained from this same library by screening with a 5' 0.2-kbp subfragment of λEF17.

Deduced amino acid sequence establishes the T11 gene as a member of the PDGF-R/CSF1-R subfamily. The complete nucleotide sequence of the 6.4-kbp cDNA of the T11 gene is shown in FIG. 3. An open reading frame beginning with a possible ATG initiation codon at nucleotide position 139 extended to a TAA termination codon at position 3406. Although the open reading frame extended further upstream, the putative initiation ATG was flanked by sequences that fulfill the Kozak criteria for an authentic initiation codon (M. Kozak, Cell 44, 283 (1986)). Moreover, the first 23 amino acid stretch displayed properties of a cleavable hydrophobic signal peptide (FIGS. 3 & 4). At the 3' end, the open reading frame was followed by ~3-kbp of untranslated sequences. A polyadenylation signal (AATAAA) was located 25 nucleotides upstream from the poly(A) sequence at the 3' end of the cDNA.

According to the putative cleavage site for the signal peptide (G. von Heijne, Nucleic Acids Res. 14, 4683 (1986)), the amino terminus of the mature product was predicted to be glutamine at amino acid 24 followed by 1066 amino acids. This polypeptide sequence with a calculated molecular mass of around 120 kd contained all of the characteristics of a membrane-spanning tyrosine kinase receptor. A hydrophobic segment consisting of 24 amino acids (residues 525 to 548) exhibited characteristics of a receptor transmembrane domain (FIGS. 3 & 4). Between the signal peptide and the transmembrane domain, there was structural homology with the extracellular ligand binding domains of the PDGF-R/CSF1-R subfamily. Ten cysteine residues were spaced at the same positions as in the other receptors of this subfamily, and eight potential N-linked glycosylation sites were distributed in its putative extracellular domain (FIG. 3).

The cytoplasmic domain was comprised of a conserved tyrosine kinase region and a hydrophilic carboxyl-terminal tail (FIGS. 3 & 4). The tyrosine kinase domain included the consensus ATP binding sequence (residues Gly-X-Gly-X-X-Gly . . . Lys) and a tyrosine residue at position 849 homologous to the major autophosphorylation site of pp60 v-src at position 416 (J. E. Smart et al., Proc. Natl. Acad. Sci USA 78, 6013 (1981)). Moreover, the tyrosine kinase was divided into two domains by a hydrophilic inter-kinase sequence as previously shown for c-fms/CSF1-R, PDGF-R, and c-kit (FIG. 4).

The amino acid homologies of its extracellular domain with those of the PDGF-R, CSF1-R, and c-kit were 31%, 18%, and 19% respectively. The two kinase domains of the T11 gene were most homologous to those of the human PDGF receptor (85% and 75%, respectively) as compared with 67 to 70% for c-fms and c-kit (FIG. 4). Even in the inter-kinase domain, its amino acid sequence was more closely aligned to the PDGF-R with 27% homology compared to 10 and 19% with c-fms or c-kit. These observations lead to the conclusion that the T11 product was in the PDGF-R/CSF1-R subfamily and most closely related to the PDGF-R.

The deduced amino acid sequence of another cDNA clone (obtained in the same experiment which produced the TR4 cDNA clone) established its product as the known human PDGF receptor. Its sequence corresponded almost completely with the recently published sequence of the known human PDGF receptor (R. G. K. Gronwald et al., ibid. 88, 3435 (1988); L. Claesson-Welsh et al., Mol. Cell. Biol. 8, 3476 (1988)). A single nucleotide difference changed residue 240 from Asn to Ser. Comparison with the mouse PDGF receptor cDNA amino acid sequence also revealed high similarities throughout all functional domains including the ligand binding domain (79%), transmembrane domain (96%), the juxtamembrane domain (97%), split tyrosine kinase domains (TK1, 99% and TK2, 97%), inter-kinase domain (86%) and carboxyl terminus (85%).

Figure 5:
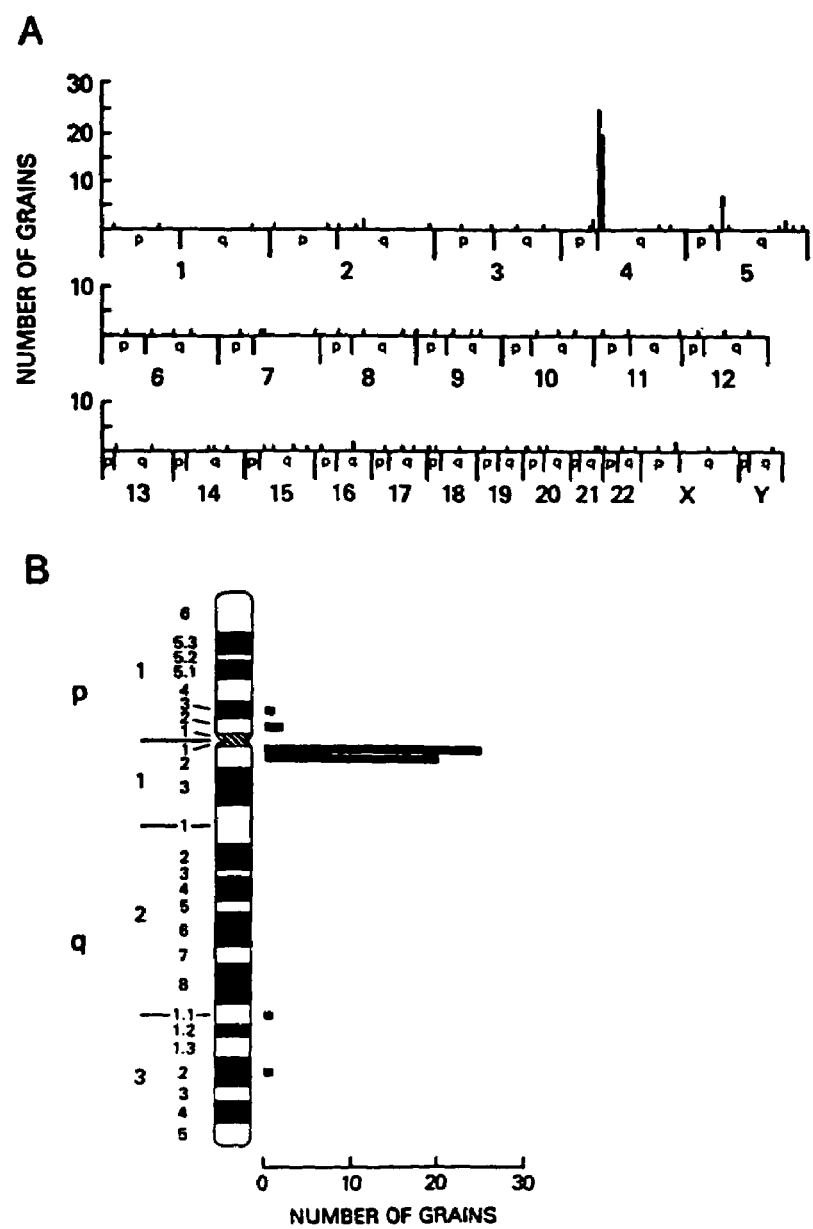
FIG. 5 shows chromosome mapping of the type α PDGF receptor gene. (A) Distribution of the silver grains on normal human chromosomes by in situ 2 hybridization with pT11-P probe (clone of the 3.6-Kbp PstI genomic fragments) (see FIG. 1). (B) Distribution of grains on chromosome 4.

Chromosomal mapping of the T11 gene. To define the new gene with respect to chromosomal location, 104 chromosome spreads were examined by in situ hybridization with a pT11-P probe. A total of 136 grains were localized on a 400-band ideogram (FIG. 5). Of the total grains, 50 (37%) were on chromosome 4 with the majority of 45 grains tightly clustered near the acentromeric region of the long arm at bands, q11-12 (FIG. 5). A second site of hybridization on chromosome 5q 11.1-11.2 consisting of 7 grains accounted for 5% of the total grains (FIG. 5).

The T11 gene probe was also hybridized to chromosomes derived from a Burkitt lymphoma cell line carrying a large abnormal marker chromosome originating from a translocation t1;5 (p 22; q23) translocation. There was no detectable labeling of the rearranged chromosome 5 in over 300 spreads examined for the presence of grains at this chromosome. Thus, in situ hybridization assigned the T11 gene to chromosome 4 at location q 11-12. This localization places the new gene within the same region as the c-kit proto-oncogene (L. d'Auriol et al., Hum. Genet 78, 374 (1988)). The structurally related genes for platelet factor 4, (C. A. Griffin et al., Cytogenetic Cell Genet 45, 67 (1987)), interferon τ-inducible factor; τIP-10, (A. D. Luster et al., Proc. Natl. Acad. Sci. USA 84, 2868 (1987)) and melanoma growth stimulatory activity (MGSA) (A. Richmond et al., EMBO J. 7, 2025 (1988)) as well as genes for α-feto protein, albumin (M. E. Harper and G. Dugaiczyk, J. Hum. Genet. 35, 565 (1983)), HPAFP (M. A. Furguson-Smith et al., Cytogenet Cell Genet 40, 628 (1985)), and the gene for dentinogenesis imperfecta have been mapped at 4q 11-13 (S. P. Ball, P. J. L. Cook, M. Mars, K. E. Buckton, Ann Hum. Genet. 46, 35 (1982)).

Expression of transcripts and protein products of the endogenous T11 gene in normal and tumor cells. To investigate the tissue specific expression of the new receptor-like gene, either of the most preferred DNAs of this invention, i.e., the HindIII-PstI 0.95-kbp fragment of the T11 genomic clone, or cDNA insert of TR4, was used for Northern blot hybridization experiments. A single 6.4-kb transcript was detected in poly(A)-containing RNAs of a variety of human tissues and cell lines. As shown in FIG. 6, relatively high levels of the transcript were found in smooth muscle, heart, and human embryo, while human liver and spleen demonstrated undetectable or barely detectable transcripts under these conditions.

Using a probe for the known human PDGF receptor gene, it was noted that the T11 and 5.3-kb PDGF-R transcripts appeared to be coexpressed at similar respective levels in each of these same tissues. Human skeletal muscle, fetal brain, placenta as well as cultured fibroblasts and glial cells also expressed high levels of both transcripts (data not shown).

Thus, the new gene and the known PDGF-R gene appeared to be coordinately expressed in normal tissues examined and exhibited a very different pattern from that reported for either c-fms/CSF1-R or c-kit (C. J. Sherr et al., Cell 41, 665 (1985); L. Coussens et al., Nature 320, 277 (1986); P. Besmer et al., ibid. 320, 415 (1986); Y. Yarden et al., EMBO J. 6, 3341 (1987)).

Expression of the T11 and PDGF-R genes were also compared in human tumor cells. Here, their patterns of expression could be readily distinguished. Several tumor cell lines were found to contain one or the other transcript but not both (FIGS. 6C and D).

Antibodies specific for either the novel or known PDGF receptor protein. In an effort to identify the protein product of the new gene, antisera to peptides were prepared based on its predicted sequence. Analogous regions of the predicted sequence of the known PDGF-R were utilized to generate antisera as well. Initial efforts to detect specific expression of the T11 gene product utilized M426 embryo fibroblast cells, from which cDNAs of both receptors had been isolated. 8387 and A204 cell lines which specifically expressed the PDGF-R or T11 gene transcripts, respectively were analyzed as well (FIG. 7A).

Western blot analysis of M426 cells with antisera (anti-T11) directed against the T11 gene product revealed 180 kd and 160 kd protein species, which were specifically competed by the immunizing peptide. The anti-PDGF-R peptide serum (designated anti-HPR) detected 180 and 165 kd proteins in the same cells. Western blot analysis of 8387 cells revealed 180 and 165 kd species, which were recognized by the anti-HPR, but not by anti-T11 serum. Conversely, A204 cells contained 180 and 160 kd species which were specifically detected by anti-T11, but not recognized by anti-HPR serum.

All of these findings indicated that these antibodies of this invention were specific for detection of the homologous receptor gene product and that T11 gene products were expressed in cells containing its transcript.

Expression of T11 cDNA in a mammalian vector system. As further test of the ability to immunologically detect the T11 gene product as well as to investigate the functional expression of its cDNA, LTR-based expression vectors were constructed for the T11 cDNA encompassing nucleotides 1 to 3454 (FIG. 3) and for the corresponding known PDGF-R cDNA as well.

Transient expression in COS-1 cells led to the specific detection of the T11 gene products as 185 kd and 160 kd species (FIG. 7B) whereas the PDGF-R appeared as 185 kd and 165 kd proteins. The respective lower MW forms of each receptor did not vary in size among the cells analyzed. However, some different sizes of the higher MW species were observed, which were likely due to cell specific differences in glycosylation.

PDGF binding to the T11 product establishes it as a new PDGF-R gene. Because of their structural and deduced amino acid sequence similarities as well as their coexpression by normal cell types known to respond to PDGF, to studies were performed to determine whether the T11 gene product exhibited any functional relationship to the known PDGF-R gene product. Thus, $^{125}$I-labeled human PDGF was incubated with control and transfected COS-1 cells in the presence or absence of unlabeled PDGF isoforms.

Figure 8:
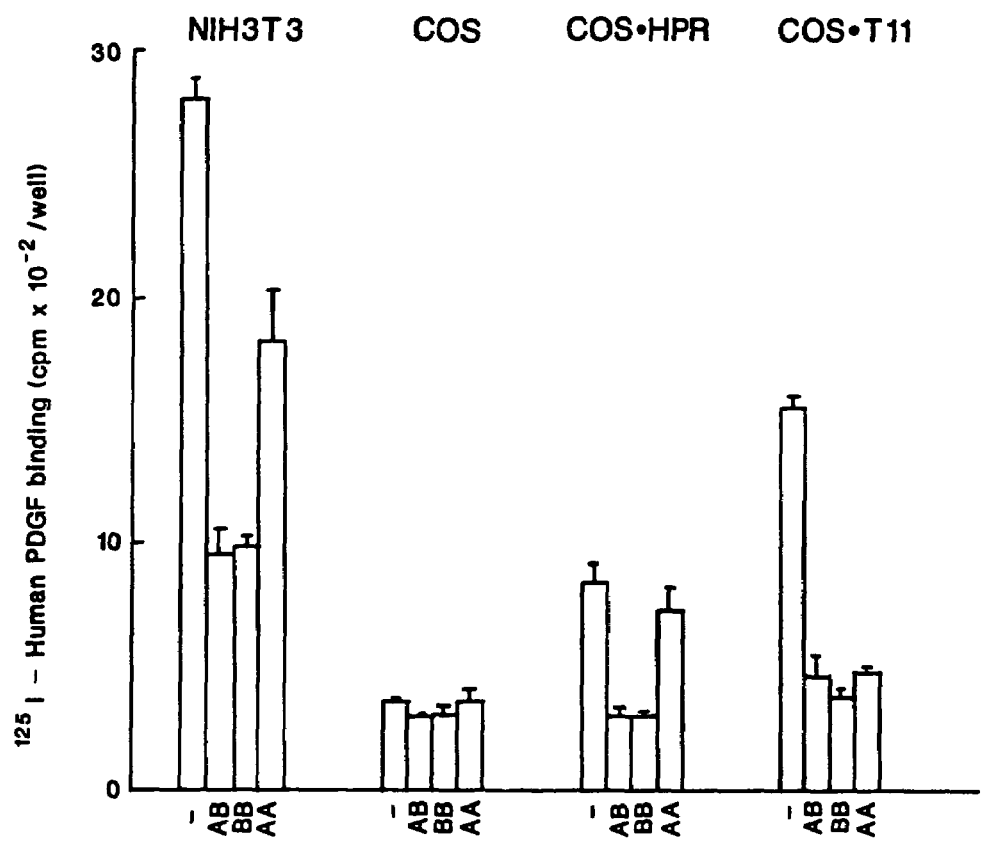
FIG. 8 displays binding of ($^{125}$I-labeled) human PDGF to mouse cells (NIH/3T3), control COS-1 cells and COS-1 cells transformed with $T_4$ cDNA or known PDGF-R cDNA expression vectors. Results represent the mean value (±SD), of triplicate samples.

As shown in FIG. 8, as much $^{125}$I-PDGF specifically bound to COS-1 cells transfected with the new receptor gene as to NIH/3T3 cells. Binding was reduced to the level of non-transfected COS-1 cells by competition with excess human PDGF (predominantly AB), PDGF-BB, or PDGF-AA. Specific binding of $^{125}$I-PDGF to COS-1 cells transfected with the PDGF-R cDNA was also observed. In this case, however, binding was competed by human PDGF (i.e., PDGF-AB) and PDGF-BB but not by PDGF-AA (FIG. 8).

Thus, while both T11 gene and PDGF-R gene products bound human PDGF, the pattern of competition by different PDGF isoforms distinguished the two receptors. These results implied that the T11 gene encoded a novel PDGF receptor with different affinities for the three dimeric forms of PDGF. Hence, the T11 receptor gene product was tentatively designated as the type α PDGF-R because PDGF binding was competed by AA as well as BB isoforms, and the product of the previously cloned PDGF receptor was designated as type β.

PDGF isoforms induce different patterns of autophosphorylation of the novel and known PDGF receptors. After PDGF binding to its receptor, a number of molecular events are rapidly triggered in vivo, including phosphorylation of the receptor protein on tyrosine residues (A. R. Frackelton, P. M. Tremble Jr., L. T. Williams, J. Biol. Chem. 259, 7909 (1984); T. O. Daniel et al., Proc. Natl., Acad. Sci. USA 82, 2684 (1985)). To compare the relative autophosphorylation of the products of the two PDGF-R genes by each PDGF isoform, the responses of A204 and 8387 cells that expressed type α and type β PDGF-R genes, respectively, were analyzed.

Figure 9:
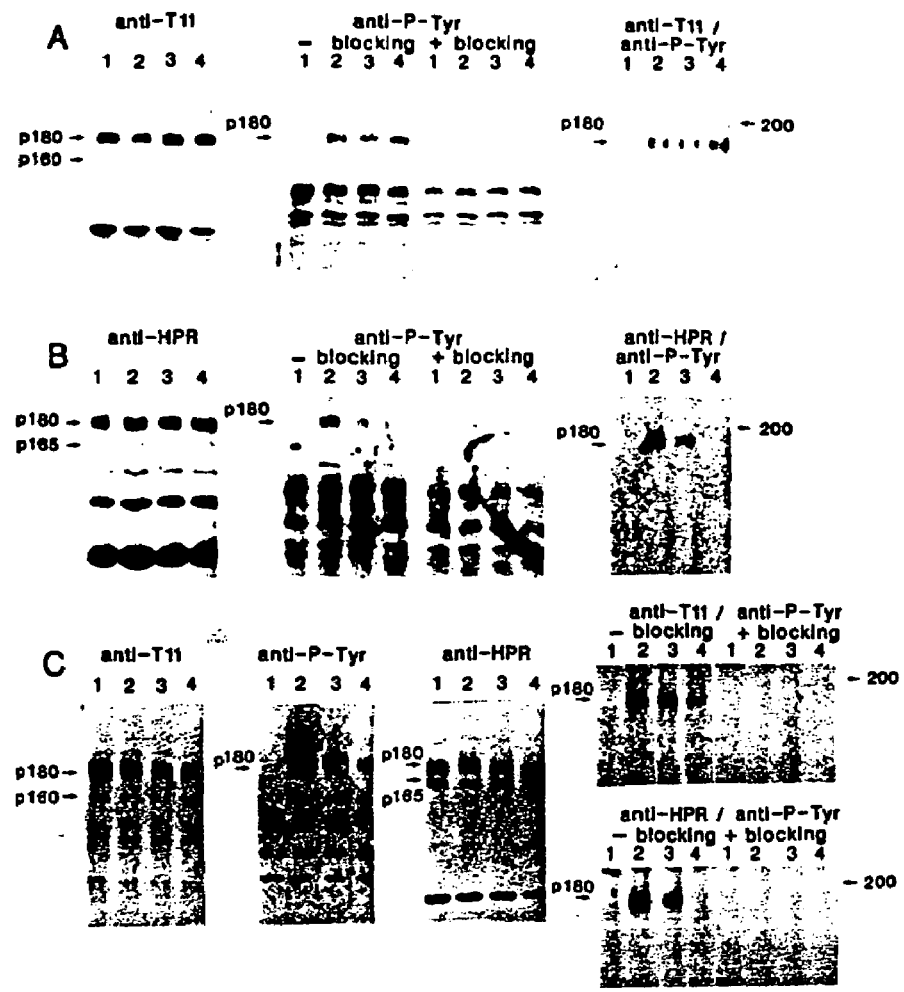
FIG. 9 demonstrates tyrosine autophosphorylation of type α and type β PDGF receptors in response to various isoforms of PDGF. A204 (A), 8387 (B), or NIH/3T3 (C) cells were incubated with PDGF-BB (30 ng/ml) (lane 2), human PDGF (30 ng/ml), (lane 3), PDGF-AA (300 ng/ml) (lane 4), or 3 nM acidic acid (vehicle control: lane 1). Cell lysates were immunoprecipitated with peptide antisera directed against predicted type α or type β PDGF receptors (anti-T11 and anti-HPR, respectively). Immunoblot analysis was with antibodies to receptors or phosphotyrosine (anti-P-Tyr) (Wang, Mol. Cell. Biol. 5: 3640 (1985)) as indicated above the blots. Arrows indicate the specific bands which were blocked in the presence of immunizing peptide.

As shown in FIG. 9A, immunoblots of A204 cells lysed 5 minutes following ligand exposure revealed readily detectable and very similar levels of autophosphorylation of a 180 kd species in response to each of the three PDGF isoforms. As further evidence that the induced autophosphorylation was specific to the type α receptor gene product, ligand stimulated A204 cell lysates were first subjected to immunoprecipitation with anti-type α PDGF-R serum (anti-T11) followed by immunoblotting with anti-phosphotyrosine serum. By this approach, it was firmly establish that the 180 kd type α PDGF receptor was phosphorylated on its tyrosine with similar intensity in response to each of the three ligands.

Exposure of 8387 cells, which expressed only the type β PDGF gene product, to the same amount of each respective PDGF isoform revealed a very different pattern of receptor autophosphorylation. Here, PDGF-BB induced the highest level of autophosphorylation of the 180 kd species specifically recognized by anti-type β PDGF-R serum (anti-HPR), and human PDGF induced detectable autophosphorylation as well (FIG. 9B). In contrast, PDGF-AA induced no detectable phosphorylation.

Thus, while PDGF-AB and PDGF-BB triggered both receptors, the much stronger response of the β type receptor to the BB homodimer as well as its lack of detectable response to the AA homodimer readily distinguished the receptors functionally.

To investigate the pattern of autophosphorylation of the two receptors by different PDGF isoforms in the same cells, NIH/3T3 cells were first triggered by different ligands followed by immunoprecipitation with either anti-type α or β PDGF-R serum. The immunoprecipitated receptor proteins were then analyzed by immunoblotting with anti-phosphotyrosine serum.

As shown in FIG. 9C, the 180 kd protein immunoprecipitated by the type α PDGF-R antiserum was phosphorylated by all three dimeric forms of PDGF. In contrast, the 180 kd phosphoprotein immunoprecipitated by the anti-type β receptor serum was detected only after human PDGF-AB or PDGF-BB stimulation. Thus, the patterns of response to different PDGF ligands remained receptor-specific in at one example of nontransformed cells naturally expressing both PDGF-R genes.

Type α PDGF receptor is more efficient in stimulating DNA synthesis in response to PDGF isoform AB. The expression of the two receptors in other fibroblast lines was analyzed next. Western blotting analysis (data not shown) revealed significant variations in the ratio of the two receptors among the lines analyzed. Whereas mouse fibroblasts expressed similar levels of type α and type β receptors, human fibroblasts such as AG1523 or M413 expressed relatively lower levels of the type α receptor than either mouse fibroblasts or M426 human fibroblasts.

Figure 10:
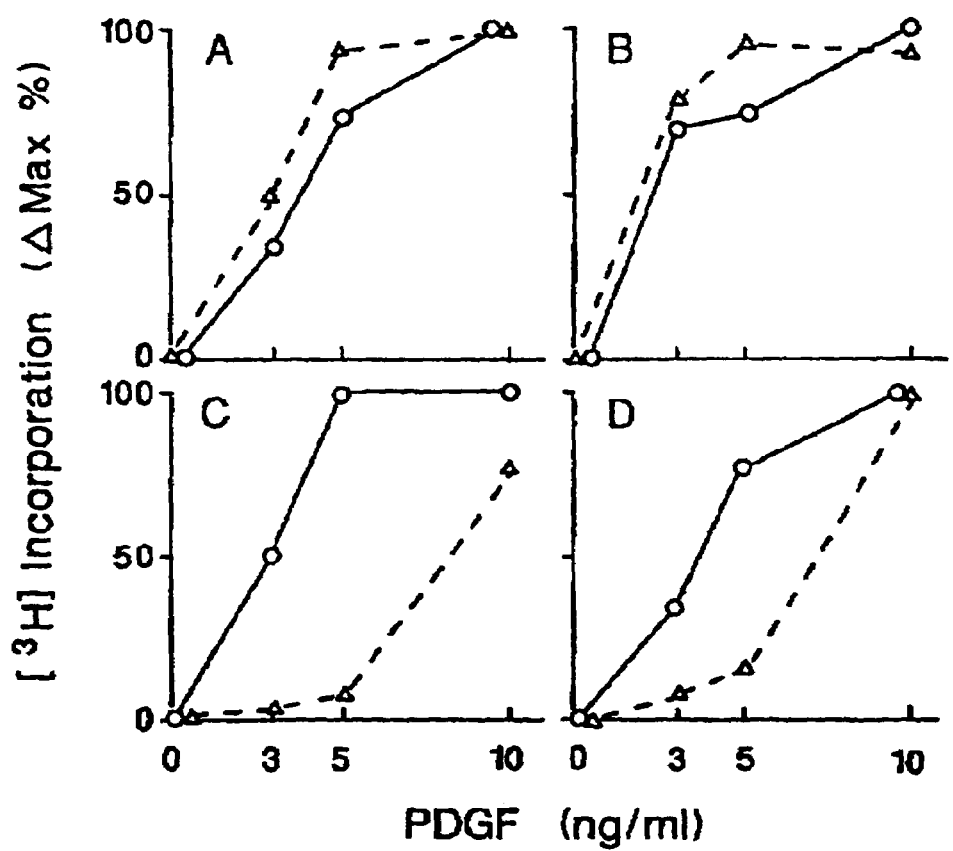
FIG. 10 shows preferential stimulation of DNA synthesis by PDGF isoform AB in various cells with higher levels of type α PDGF receptor than type β receptor. Stimulation of DNA synthesis by PDGF-AB (triangles) or PDGF-BB (circles) in various cell lines is shown as follows: (A) mouse NIH/3T3; (B) human M426; (C) human AG1523; and (D) human M413.

Saturating amounts of PDGF-AB or PDGF-BB yielded similar increases in DNA synthesis in each of the cell lines (data not shown). However, submaximal doses of PDGF-AB and PDGF-BB showed significant differences in the levels of mitogenic activity observed (FIG. 10). Whereas, NIH/3T3, BALB/3T3 and M426 cells responded with comparable efficiency to PDGF-BB and AB, PDGF-AB was significantly less active on AG1523 or M413 cells. Their lesser mitogenic responsiveness to PDGF-AB seemed to correlate with the high ratio of β to α receptors in these cells detected immunologically.

Taken together with the dose-response curves observed for phosphorylation of the two receptors in NIH/3T3 cells by the different PDGF isoforms, these results strongly suggested preferential triggering of the type α receptor, in the presence of the type β receptor, by PDGF-AB, as well as by PDGF-AA.

Independent expression of two PDGF gene types after introduction of cDNAs into PDGF receptor-free hematopoietic cells. To investigate the biological and biochemical responses specific to each PDGF-R gene product, systems were developed to look at this receptor in cells in which each type could be independently introduced and expressed. These systems were based on the 32D cell line, a mouse hematopoietic cell line normally dependent on Il-3 for survival and proliferation. Recent studies have established that introduction of an expression vector for the EGF-R in these cells led to effective coupling with EGF mitogenic signal transduction pathways.

The mammalian expression vectors described above, carrying the gpt selectable marker, was used to transfect 32D cells with either the type α or the type β PDGF-R cDNAs by electroporation. Transformants were selected using medium supplemented with mycophenolic acid. After 2 weeks in the selective medium, viable cultures were obtained.

Cultures designated 32D-αR and 32D-βR, respectively were subjected to Northern blot analysis, as described above. Neither type of PDGF-R mRNA was detectable in the parental 32D cells even under relaxed hybridization conditions, which conditions enabled detection of the respective mouse PDGF-R gene transcripts in NIH/3T3 fibroblasts. In contrast, 32-αR and 32D-βR transfectants expressed abundant transcripts specific to the human type α and type β PDGF-R genes, respectively. When membranes lysates of these transfectant were subjected to immunoblot analysis, anti-type α PDGF-R peptide serum detected 180 kd and 160 kd protein species in 32D-αR but not in 32D-β cells. Moreover, these proteins were specifically competed by the immunizing peptide. Conversely, 32D-βR cells contained 180-200 kd and a 165 kd species which were specifically detected by the anti-type β PDGF-R serum. None of these proteins species were detectable in control 32D cells.

Figure 11:
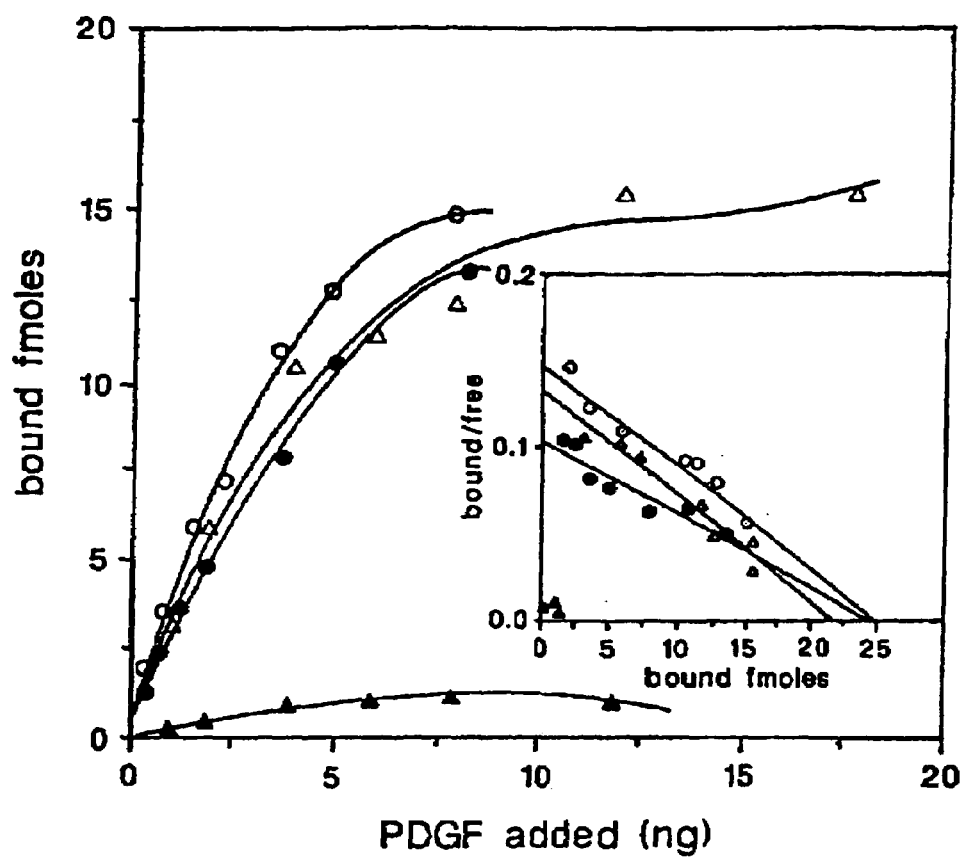
FIG. 11 presents binding data for type α and type β PDGF receptors on (human 32D) cells transfected with vectors bearing the respective cDNAs, demonstrating that the type β receptor shows a strikingly lower affinity for the PDGF-AB form. Receptor binding of PDGF-AB (triangles) or PDGF-BB (circles) by human D32 cells were reconstituted with type α (open symbols) or type β (filled symbols) PDGF receptors by transfection with vectors bearing the respective cDNA. The inset displays the same data replotted in the standard (semi-log) Scatchard format.

Type α receptor has a higher binding affinity for the PDGF-AB isoform. PDGF-BB binding was compared in 32D-αR or 32D-βR transfectants, and both showed high affinity binding. Scatchard analysis revealed about two thousand receptors per cell with a single affinity class of binding sites. The $K_d$s were 0.4 nM and 0.5 nM for 32D-αR and 32D-βR cells, respectively (FIG. 11). 32D-αR cells also showed a high binding affinity ($K_d$=0.4 nM) for $^{125}$I-PDGF-AB, exhibiting the same number of binding sites as for PDGF-BB.

In contrast, however, 32D-βR cells revealed ten times less binding capacity for $^{125}$I-PDGF-AB than did 32D-αR cells. Thus, standardized on the basis of their similar binding of PDGF-BB, the type β receptor showed a strikingly lower affinity for PDGF-AB.

Common biological functions independently triggered by type α and β PDGF gene products. Mitogenesis and chemotaxis are among the most well characterized responses of fibroblasts to PDGF. Thus, whether 32D-αR or βR lines mediated either of these biological responses was investigated.

Figure 12:
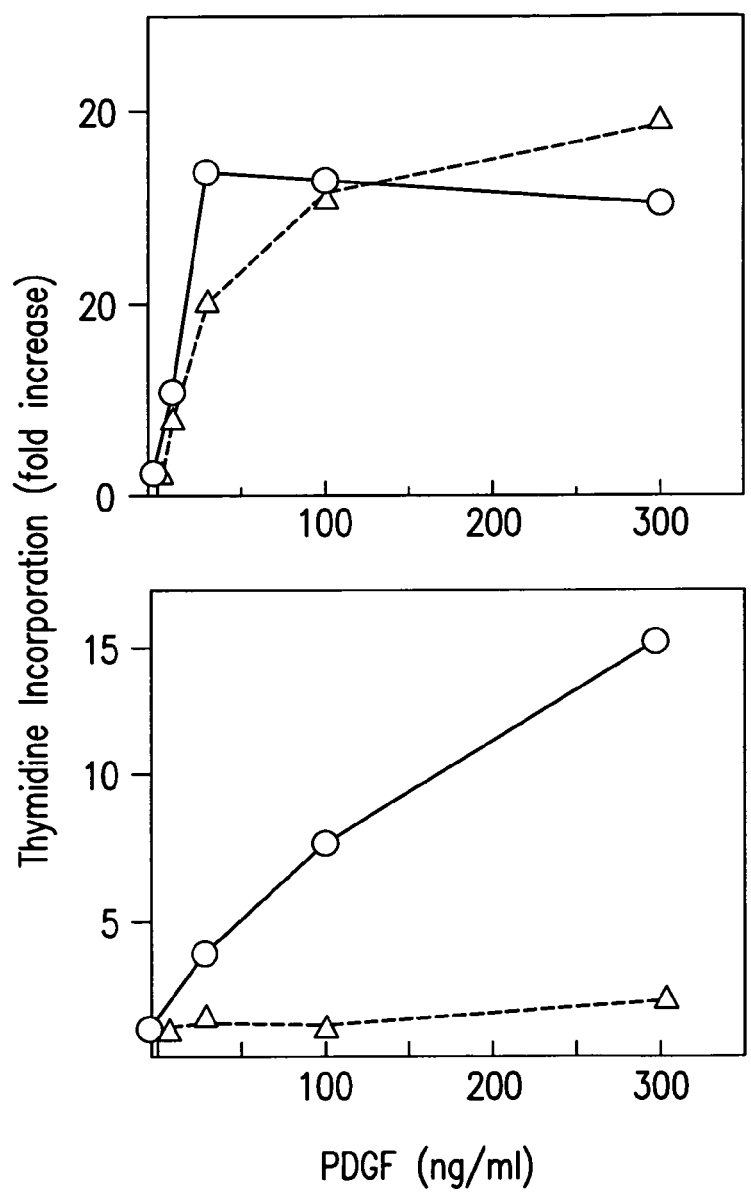
FIG. 12 illustrates the similar mitogenic responses to PDGF-BB by cells containing either type α or type β PDGF-R and the significantly lesser DNA synthesis response to PDGF-AB in the type β, compared to type α receptor containing cells. DNA synthesis stimulation responses to PDGF-AB (triangles) or PDGF-BB (circles) by human D32 cells shown reconstituted with type a (upper panel) or type β (lower panel) PDGF receptors.

Growth of 32D cells is normally strictly dependent on interleukin 3 (hereinafter, IL-3), and deprivation of IL-3 from the medium led to the rapid loss of viability both of the transfectants and the control 32D cells. As shown in FIG. 12, PDGF-BB was able to couple efficiently with mitogenic signal transduction pathways and abrogate IL-3 dependence in a similar dose dependent manner in both transfectants, but had no effect in control 32D cells. Thus, the presence of either type α or β PDGF-R was both necessary and sufficient for the mitogenic response to PDGF BB.

However, whereas, the type α receptor containing 32D cells were as responsive to PDGF-AB as to PDGF-BB, PDGF-AB elicited a significantly lesser DNA synthesis response in 32D-βR cells (FIG. 12).

These findings were confirmed by analysis of colony-formation in semi-solid agar containing medium. Both transfectants formed colonies readily in PDGF-BB, supplemented medium but only 32D-αR cells did so in medium supplemented with PDGF-AB (data not shown). Thus, the mitogenic responses observed with both 32D-αR and βR transfectants correlated well with the binding properties of the same PDGF isoforms to α and β receptors expressed by each cell line, respectively.

Figure 13:
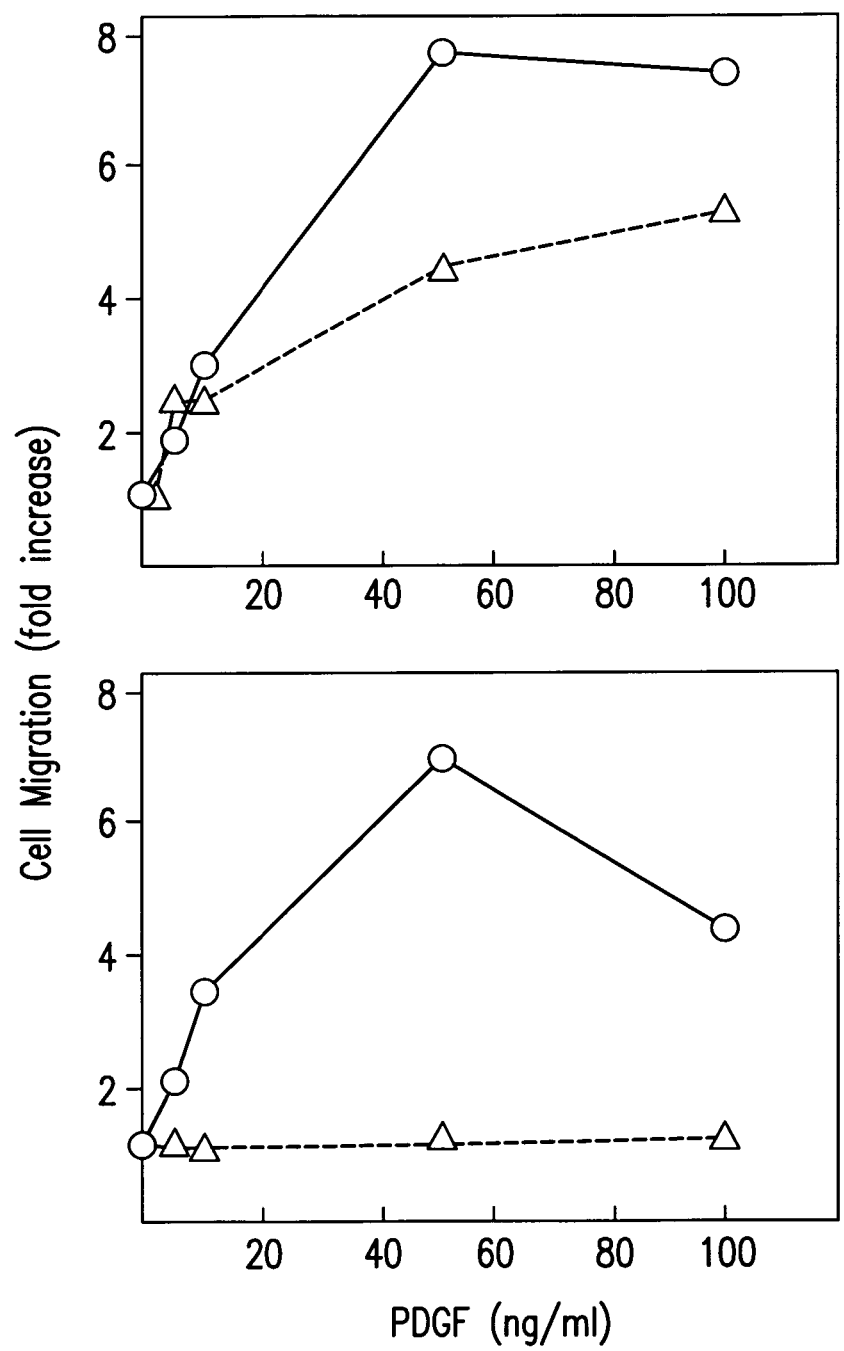
FIG. 13 demonstrates equivalent chemotaxic cellular responses to PDGF-BB in cells with type α or β PDGF-R, whereas PDGF-AB elicited a considerably lower chemotaxic response with type β receptors than with type a receptors. Chemotaxic responses to PDGF-AB (triangles) or PDGF-BB (circles) by human D32 cells are shown reconstituted with type a (upper panel or type β (lower panel) PDGF receptors.

To address whether chemotaxis was specifically mediated by either type α or β PDGF receptors, a chemotaxis assay was employed using the modified Boyden chamber technique well known in the art. While 32D cells lacking PDGF receptors did not respond to PDGF-AB or PDGF-BB, PDGF-BB was chemotaxic for both α and β receptor expressing transfectants. PDGF-AB was relatively more active on 32D-αR cells (FIG. 13).

Thus, each PDGF receptor independently coupled with both mitogenic and chemotaxis signalling pathways inherently present in 32D cells. Moreover, these biological functions were triggered according to the relative binding abilities of PDGF isoforms to either receptor.

Inositol lipid metabolism and cytosolic $Ca^{2+}$ mobilization coupling with independently reconstituted receptors. Recent investigations have suggested an important role of receptor-mediated. turnover of inositol lipids resulting in the increase of second messengers such as intracellular free calcium and diacyloglycerol in the transduction of the PDGF-induced mitogenic-signal. Thus, the effects of PDGF-AB and PDGF-BB on inositol lipid metabolism and intracellular free $Ca^{2+}$ ($[Ca^{2+}]i$) were studied in type α and type β PDGF-R containing 32D cells.

The accumulation of radioactive inositol phosphates was measured after prelabelling cultures with $^3$H-myoinositol and challenge with PDGF isoforms at 37° C. in the presence of LiCl, according to methods well known in the art. $[Ca^{2+}]i$ was measured in 32D cells in suspension, loaded with the fluorescent $[Ca^{2+}]i$ indicator fura-2, and treated with PDGFs in the complete incubation medium.

Figure 14:
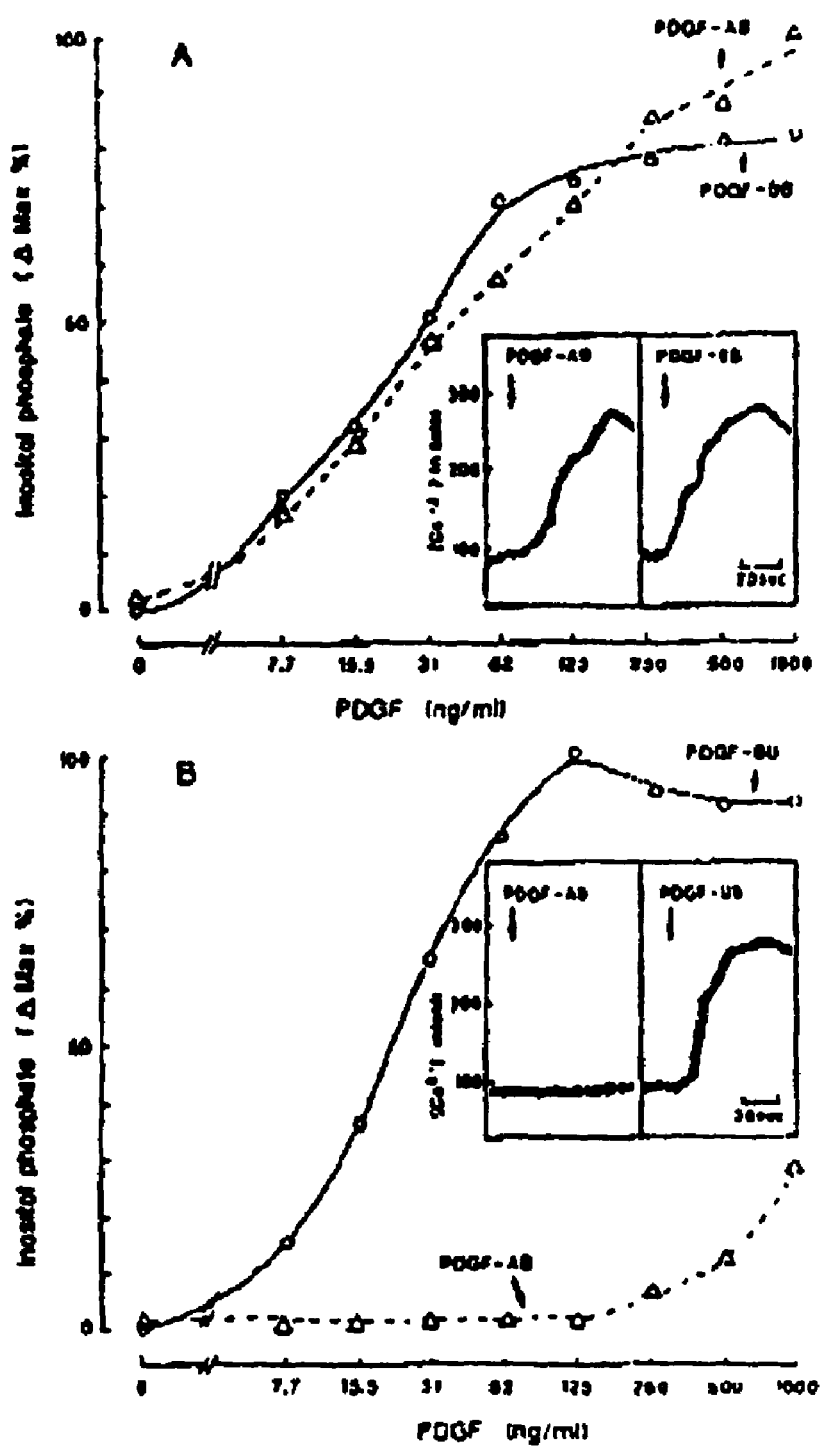
FIG. 14 shows the effect of PDGF-AB and PDGF-BB on inositol phosphate formation and cytosolic calcium mobilization ($[Ca^{2+}]i$) in cells bearing type α and type β PDGF-R, with the type α receptors again responding more efficiently to PDGF-AB. Responses of inositol phosphate formation and cytosolic calcium iron mobilization (i.e., $[CA^{2+}]i$; data in insets) to human PDGF-AB (triangles) or PDGF-BB (circles) by human D32 cells are shown reconstituted with type α (upper panel) or type β (lower panel) PDGF receptors.

FIG. 14 shows the effect of PDGF-AB and PDGF-BB on inositol phosphate formation and $[Ca^{2+}]i$ in type α and type β PDGF-R 32D cells. As shown in FIG. 14 (panel A), both PDGF-BB and PDGF-AB were able to elicit dose-dependent accumulation of inositol phosphates, with similar relative potencies. The same isoforms exerted almost identical increases in $[Ca^{2+}]i$ in type α PDGF-R 32D cells as wells (FIG. 14, panel A, insert). PDGF-BB also markedly stimulated inositol lipid metabolism and intracellular $Ca^{2+}$ mobilization in type β PDGF-R 32D cells, establishing the very similar biochemical responses elicited by these distinct PDGF-R gene products in 32D cells in response to PDGF-BB.

FIG. 14 (panel B) shows that PDGF-AB was significantly less effective than PDGF-BB in promoting inositol phosphate accumulation in type β PDGF-R 32D cells. Detectable release of inositol phosphate occurred only at high PDGF-AB concentration. Similarly, PDGF-AB elicited little or no $(Ca^{2+})i$ response.

DISCUSSION

The present studies demonstrate the existence of two distinct human PDGF receptor genes. Further, they illustrate the detection and isolation of two principal embodiments of this invention, the genomic and cDNA clones of a novel gene within the PDGF-R/CSF1-R subfamily. This gene is divergent from but most closely related to the known PDGF-R gene. Under conditions of natural expression as well as following introduction of this novel cDNA into appropriate target cells by means of an expression vector, functional responses of its product to PDGF were demonstrated at concentrations that bound and triggered tyrosine phosphorylation of the previously identified PDGF receptor.

Standardized on the basis of similar levels of tyrosine phosphorylation (and several other activities) of PDGF-R gene product induced by a constant amount of PDGF, the new receptor was shown to respond better than the known PDGF-R to the AA homodimer. Conversely, the known receptor responded preferentially to the BB homodimer.

Based upon the present findings, the new gene product has been designated as the type α PDGF-R and the previously identified PDGF-R gene product as the type β receptor.

The AA homodimer failed to stimulate detectable tyrosine phosphorylation of the β type receptor in NIH/3T3 cells and yqt is capable of inducing DNA synthesis in this cell line (P. Beckman et al., Science 241, 1346 (1988)). This indicated that the α type receptor can couple with mitogenic signalling pathways in fibroblasts. The β type receptor has also been reported to couple PDGF with mitogenic pathways (J. A. Escobedo et al., ibid. 240, 1532 (1988)). These results suggested that both receptor gene products can induce a proliferative response.

The ability, according to compositions and methods of this invention, to stably introduce expression vectors for these distinct receptor genes into a null cell made it possible to confirm this suggestion in human cells. Further studies in such cells showed that other known PDGF functions including chemotaxis (H. Seppa et al., J. Cell Biol. 92, 584 (1982); G. R. Grotendorst et al., J. Cell Physiol. 113, 261 (1982); T. F. Deuel, R. M. Senior, J. S. Huang, G. L. Griffin, J. Clin. Invest. 69, 1046 (1982)) membrane ruffling (K. Mellstrom et al., J. Cell Motility and Muscle Res. 4, 589 (1983)), as well as transmodulation of a heterologous receptor (E. Rozengurt, M. Rodriquez-Pnena, K. A. Smith, Proc. Natl. Acad. Sci. USA 80, 7244 (1983); R. J. Davis and M. P. Czech, ibid. 82, 4080 (1985)), are not specifically mediated by either type α or β PDGF-R gene products.

Such knowledge is a necessary prelude to understanding and diagnosis of disease conditions affecting these PDGF functions, which can be furthered through additional practice of the present invention.

Among human tumor cell lines analyzed using methods of this invention, several were observed in which there was discoordinate expression of the two PDGF-R genes. Moreover, representative tumor cell lines expressing mRNA from either gene were shown to contain the respective protein product, which bound and was phosphorylated on tyrosine in response to PDGF.

The availability of the immunologic as well as the molecular probes of this invention, specific for either type α or type β PDGF-R gene products, makes it possible to identify human tumors in which expression of the PDGF-A or B chain, in combination with either receptor gene, may be causally implicated in tumor development. At the same time, the availability of reagents for specific detection of each type of component is a critical aid in efforts to implicate the abnormal expression of this complex growth factor-receptor network in other chronic disease states such as arteriosclerosis, arthritis, and fibrotic diseases (R. Ross, E. W. Raines, D. F. Bowen-Pope, Cell 46, 155 (1986)) Plasmids HF1 and H815 were deposited at the American Type Culture Collection and have accession numbers 75058 and 75059, respectively.

Additional observations of scientific import have already been provided by the practice of the invention as herein described. For instance, the chromosomal location of the novel gene, established using DNAs of this invention, provides insight into the possible evolution of this receptor gene family. Thus, the chromosomal localization places the type α PDGF receptor gene on chromosome 4 at 4q 11-12, the same region as c-kit (L. d'Auriol et al., Hum. Genet 78, 374 (1988)), a related receptor-like gene. Other genes of this subfamily have been localized on chromosome 5. These include the type β PDGF-R mapped at 5q 23-31 (Y. Yarden et al., Nature 323, 226 (1986)) and the CSF1-R gene, on 5q 33.2-33.3 (M. M. Le Beau et al., ibid. 231, 984 (1986)). There is evidence for a common ancestral origin of human chromosomes 4 and 5 (D. E. Comings, Nature 238, 455 (1972)). These related receptor genes cluster near the centromere on 4q or at the distal half of 5q. Thus, if the progenitor(s) of these genes were confined to a single ancestral chromosome, the breakup of linkage might be explained by an inversion within the long arm.

The present studies also establish that different PDGF-R genes encode two receptor types, with binding properties evidently independent of the cell in which each is expressed. The implications of this observation can be better appreciated in light of knowledge about other receptor systems.

There is emerging evidence that as more complex organisms have evolved, mechanisms of intercellular communication have increased in complexity as well. The related EGF and TGF$_\alpha$ molecules interact with simila affinities with a common receptor, the EGF receptor (J. Massague, J. Biol. Chem. 258, 13614 (1983)). Different patterns of developmental and tissue expression of these growth factors (R. Derynck et al., Cancer Res. 47, 707 (1987); D. C. Lee et al., Mol. Cell. Biol. 5, 3644 (1985); D. R. Twardzik, Cancer Res. 45, 5413 (1985); R. J. Coffey et al., Nature 328, 817 (1987)) presumably account for their present existence.

There are increasing examples of evolutionarily divergent receptor genes as well. The products of such genes can respond to completely different ligands, as is the case of PDGF and CSF-1 receptors (E. S. Kawasaki et al., Science 230 291 (1985); C. Betsholtz et al., Nature 320, 695 (1986)), or, alternatively, to related ligands, as with the IGF-I and insulin receptors (A. Ullrich et al., Nature 313 (1985); Y. Ebina et al., Cell 40, 747 (1985); A. Ullrich et al., EMBO J. 5, 2503 (1986)). Here the developmental and tissue specific expression of both the receptors and their ligands, as well as the biochemical responses triggered, have evolved with the complexity of the organism.

As demonstrated in the present studies, the responses mediated by PDGF not only involve different dimeric forms of the related ligands encoded by two genes, but two related genes encoding different PDGF receptors as well. In addition to their differences in tissue specific expression (C. Betsholtz et al., Nature 320, 695 (1986); R. A. Seifert, S. M. Schwartz, D. F. Bowen-Pope, Nature 34, 669 (1984); M. Jaye et al., Science 228, 882 (1985); J. Nilsson et al., Proc. Natl. Acad. Sci. USA 82, 4418 (1985); T. Collins et al., Nature 316, 748 (1985)), the two PDGF gene products are known differ in their relative secretory capacity. The PDGF-A chain is much more efficiently released than is the B chain (P. Beckman et al., Science 241, 1346 (1988)), giving the former the possibility of acting at greater distances.

In view of the present evidence of coordinate expression of the two PDGF receptor genes in all normal tissues so far examined, their tissue specific expression may not be a major determinant of their functions. However, application of the methods of the present invention to a comprehensive survey of the expression of each receptor type during embryonic development and in homogeneous normal cell populations may uncover evidence of differential regulation.

For purposes of completing the background description and present disclosure, each of the published articles, patents and patent applications heretofore identified in this specification are hereby incorporated by reference into the specification.

The foregoing invention has been described in some detail for purposes of clarity and understanding. It will also be obvious that various combinations in form and detail can be made without departing from the scope of the invention.

What is claimed is:

1. A substantially pure form of human type α-platelet derived growth factor receptor (α PDGFR) protein having the amino acid sequence selected from the group consisting of
   a) amino acids 1-1089 of FIG. 3; and
   b) amino acids 24-1089 of FIG. 3.

2. A substantially pure form of human α PDGFR protein according to claim 1, wherein the receptor protein contains a signal peptide and has the amino acid sequence of amino acids 1-1089 as shown in FIG. 3.

3. A substantially pure form of human α PDGFR protein according to claim 1, wherein the receptor protein has the amino acid sequence of amino acids 24-1089 as shown in FIG. 3.

4. A cDNA encoding a human α platelet-derived growth factor receptor (α PDGFR) protein wherein said cDNA hybridizes under stringent conditions with a DNA probe selected from the group consisting of:
   a) the cDNA T11 having a nucleotide sequence beginning at nucleotide 1 and ending at nucleotide 3454 as shown in FIG. 3;
   b) the cDNA TR4 containing a nucleotide sequence encoding a signal peptide and having an open reading frame beginning at nucleotide 139 and extending to a TAA termination codon at nucleotide 3406 as shown in FIG. 3;
   c) The cDNA TR4 which does not contain a nucleotide sequence encoding a signal peptide and having the nucleotide sequence beginning at nucleotide 208 and ending at nucleotide 3406 as shown in FIG. 3; and
   d) The cDNA contained in pHF1 as shown in FIG. 2 and having a nucleotide sequence beginning at nucleotide 2568 and ending at nucleotide 6378 as shown in FIG. 3.

5. The cDNA encoding a human a PDGFR protein according to claim 4, wherein said receptor protein has the amino acid sequence selected from the group consisting of
   amino acids 24-1089 as shown in FIG. 3.

6. The cDNA encoding a human α PDGFR protein according to claim 5, wherein the amino acids which represent the signal peptide have been cleaved and the receptor protein has the amino acid sequence 24 to 1089 as shown in FIG. 3.

7. The cDNA T11 according to claim 4 having a nucleotide sequence beginning at nucleotide 1 and ending at nucleotide 3454 as shown in FIG. 3.

8. The cDNA TR4 according to claim 4 containing a nucleotide sequence encoding a signal peptide and having an open reading frame beginning at nucleotide 139 and extending to a TAA termination codon at nucleotide 3406 as shown in FIG. 3.

9. A cDNA TR4 according to claim 4 which does not contain a nucleotide sequence encoding a signal peptide and having the nucleotide sequence beginning at nucleotide 208 and ending at nucleotide 3406 as shown in FIG. 3.

10. The cDNA contained in pHF1 according to claim 4 and having a nucleotide sequence beginning at nucleotide 2568 and ending at nucleotide 6378 as shown in FIG. 3.

11. The cDNA of claim 4, wherein said polynucleotide is the cDNA insert contained in plasmid pHF1, deposited under ATCC accession No. 75058.

12. Plasmid pHF1 deposited under ATCC accession No. 75058.

13. A recombinant DNA vector comprising the cDNA according to any one of claims 11, 4, 5, 6, 7, 8, 9 or 10.

14. An in vitro culture of cells transformed with the cDNA according to any one of claims 11, 4, 5, 6, 7, 8, 9 or 10.

15. A method of producing a human type α-platelet derived growth factor receptor (α PDGFR) protein comprising culturing cells according to claim 14 under conditions such that said protein is produced and isolating said protein from said cells.

* * * * *

UNITED STATES PATENT AND TRADEMARK OFFICE
CERTIFICATE OF CORRECTION

| | | |
|---|---|---|
| PATENT NO. | : 7,427,671 B1 | Page 1 of 3 |
| APPLICATION NO. | : 08/439095 | |
| DATED | : September 23, 2008 | |
| INVENTOR(S) | : Toshimitsu Matsui, Stuart A. Aaronson and Jacalyn H. Pierce | |

It is certified that error appears in the above-identified patent and that said Letters Patent is hereby corrected as shown below:

Title Page; item (57);
ABSTRACT: line 6, before the words "platelet derived growth factor" delete "a" and substitute --α--.

FIGURE 3: delete "See Legend on next page".

FIGURE 6: delete "See Legend on next page".

Column 5, line 18, insert --.-- between the words "analyses" and "Hybridization".

Column 5, line 20, delete "lane" and substitute --lanes--.

Column 5, line 21, delete "lane" and substitute --lanes-- in two separate places.

Column 5, line 23, delete "EchoRI" and substitute --EcoRI--.

Column 5, line 27, delete "[lambda]T11" and substitute --λT11--.

Column 5, line 34, delete "$T_4$" and substitute --TR4--.

Column 5, line 40, delete "cystine" and substitute --cysteine--.

Column 5, line 46, delete "the $T_4$ cDNA" and substitute --a circle over the Tyr--.

Column 5, line 46, delete "T11" and substitute --λT11--.

Column 5, line 48, insert --is-- between the words "box" and "close".

Column 5, line 48, insert --to-- between the words "close" and "the".

UNITED STATES PATENT AND TRADEMARK OFFICE
CERTIFICATE OF CORRECTION

| | |
|---|---|
| PATENT NO. | : 7,427,671 B1 |
| APPLICATION NO. | : 08/439095 |
| DATED | : September 23, 2008 |
| INVENTOR(S) | : Toshimitsu Matsui, Stuart A. Aaronson and Jacalyn H. Pierce |

It is certified that error appears in the above-identified patent and that said Letters Patent is hereby corrected as shown below:

Column 5, lines 49 and 50, delete "is underlined as well".

Column 5, line 60, delete "is" and substitute --as--.

Column 5, line 60, delete "refer" and substitute --refers--.

Column 6, line 24, delete "$T_4$" and substitute --TR4--.

Column 6, line 43, delete "acidic" and substitute --acetic--.

Column 7, line 12, delete "a" and substitute --α--.

Column 7, line 15, delete "a" and substitute --α--.

Column 7, line 15, delete "panel" and substitute --panel)--.

Column 12, line 12, delete "T" between the words "method" and "specific" and substitute --to--.

Column 14, line 1, delete "λTa11" and substitute --λT11--.

Column 17, line 15, delete "to".

Column 18, line 23, insert --least-- between the words "at" and "one".

Column 19, lines 11 and 12, delete "transfectant" and substitute --transfectants--.

Column 20, line 33, delete "wells" and substitute --well--.

Column 21, line 6, delete "yqt" and substitute --yet--.

UNITED STATES PATENT AND TRADEMARK OFFICE
CERTIFICATE OF CORRECTION

PATENT NO. : 7,427,671 B1
APPLICATION NO. : 08/439095
DATED : September 23, 2008
INVENTOR(S) : Toshimitsu Matsui, Stuart A. Aaronson and Jacalyn H. Pierce It is certified that error appears in the above-identified patent and that said Letters Patent is hereby corrected as shown below:

Column 21, line 52, delete "H815" and substitute --HB15--.

Column 22, line 45, insert --to-- between the words "known" and "differ".

Claim 5, column 34, line 59, delete "a" between the words "human" and "PDGFR" and substitute --α--.

Signed and Sealed this

Eighth Day of September, 2009

David J. Kappos
*Director of the United States Patent and Trademark Office*

SEQUENCE LISTING

<160> NUMBER OF SEQ ID NOS: 2

<210> SEQ ID NO 1
<211> LENGTH: 1089
<212> TYPE: PRT
<213> ORGANISM: Artificial Sequence
<220> FEATURE:
<223> OTHER INFORMATION: Description of Artificial Sequence:/note =
      Synthetic Construct

<400> SEQUENCE: 1

```
Met Gly Thr Ser His Pro Ala Phe Leu Val Leu Gly Cys Leu Leu Thr
 1               5                  10                  15

Gly Leu Ser Leu Ile Leu Cys Gln Leu Ser Leu Pro Ser Ile Leu Pro
            20                  25                  30

Asn Glu Asn Glu Lys Val Val Gln Leu Asn Ser Ser Phe Ser Leu Arg
        35                  40                  45

Cys Phe Gly Glu Ser Glu Val Ser Trp Gln Tyr Pro Met Ser Glu Glu
    50                  55                  60

Glu Ser Ser Asp Val Glu Ile Arg Asn Glu Glu Asn Asn Ser Gly Leu
65                  70                  75                  80

Phe Val Thr Val Leu Glu Val Ser Ser Ala Ser Ala Ala His Thr Gly
                85                  90                  95

Leu Tyr Thr Cys Tyr Tyr Asn His Thr Gln Thr Glu Glu Asn Glu Leu
            100                 105                 110

Glu Gly Arg His Ile Tyr Ile Tyr Val Pro Asp Pro Asp Val Ala Phe
        115                 120                 125

Val Pro Leu Gly Met Thr Asp Tyr Leu Val Ile Val Glu Asp Asp Asp
    130                 135                 140

Ser Ala Ile Ile Pro Cys Arg Thr Thr Asp Pro Glu Thr Pro Val Thr
145                 150                 155                 160

Leu His Asn Ser Glu Gly Val Val Pro Ala Ser Tyr Asp Ser Arg Gln
                165                 170                 175

Gly Phe Asn Gly Thr Phe Thr Val Gly Pro Tyr Ile Cys Glu Ala Thr
            180                 185                 190

Val Lys Gly Lys Lys Phe Gln Thr Ile Pro Phe Asn Val Tyr Ala Leu
        195                 200                 205

Lys Ala Thr Ser Glu Leu Asp Leu Glu Met Glu Ala Leu Lys Thr Val
    210                 215                 220

Tyr Lys Ser Gly Glu Thr Ile Val Val Thr Cys Ala Val Phe Asn Asn
225                 230                 235                 240

Glu Val Val Asp Leu Gln Trp Thr Tyr Pro Gly Glu Val Lys Gly Lys
                245                 250                 255

Gly Ile Thr Met Leu Glu Glu Ile Lys Val Pro Ser Ile Lys Leu Val
            260                 265                 270

Tyr Thr Leu Thr Val Pro Glu Ala Thr Val Lys Asp Ser Gly Asp Tyr
        275                 280                 285

Glu Cys Ala Ala Arg Gln Ala Thr Arg Glu Val Lys Glu Met Lys Lys
    290                 295                 300

Val Thr Ile Ser Val His Glu Lys Gly Phe Ile Glu Ile Lys Pro Thr
305                 310                 315                 320

Phe Ser Gln Leu Glu Ala Val Asn Leu His Glu Val Lys His Phe Val
                325                 330                 335

Val Glu Val Arg Ala Tyr Pro Pro Pro Arg Ile Ser Trp Leu Lys Asn
```

-continued

```
                340                 345                 350
Asn Leu Thr Leu Ile Glu Asn Leu Thr Glu Ile Thr Thr Asp Val Glu
                    355                 360                 365
Lys Ile Gln Glu Ile Arg Tyr Arg Ser Lys Leu Lys Leu Ile Arg Ala
            370                 375                 380
Lys Glu Glu Asp Ser Gly His Tyr Thr Ile Val Ala Gln Asn Glu Asp
385                 390                 395                 400
Ala Val Lys Ser Tyr Thr Phe Glu Leu Leu Thr Gln Val Pro Ser Ser
                405                 410                 415
Ile Leu Asp Leu Val Asp Asp His His Gly Ser Thr Gly Gly Gln Thr
            420                 425                 430
Val Arg Cys Thr Ala Glu Gly Thr Pro Leu Pro Asp Ile Glu Trp Met
                435                 440                 445
Ile Cys Lys Asp Ile Lys Lys Cys Asn Asn Glu Thr Ser Trp Thr Ile
            450                 455                 460
Leu Ala Asn Asn Val Ser Asn Ile Ile Thr Glu Ile His Ser Arg Asp
465                 470                 475                 480
Arg Ser Thr Val Glu Gly Arg Val Thr Phe Ala Lys Val Glu Glu Thr
                485                 490                 495
Ile Ala Val Arg Cys Leu Ala Lys Asn Leu Leu Gly Ala Glu Asn Arg
            500                 505                 510
Glu Leu Lys Leu Val Ala Pro Thr Leu Arg Ser Glu Leu Thr Val Ala
        515                 520                 525
Ala Ala Val Leu Val Leu Leu Val Ile Val Ile Ile Ser Leu Ile Val
    530                 535                 540
Leu Val Val Ile Trp Lys Gln Lys Pro Arg Tyr Glu Ile Arg Trp Arg
545                 550                 555                 560
Val Ile Glu Ser Ile Ser Pro Asp Gly His Glu Tyr Ile Tyr Val Asp
                565                 570                 575
Pro Met Gln Leu Pro Tyr Asp Ser Arg Trp Glu Phe Pro Arg Asp Gly
                580                 585                 590
Leu Val Leu Gly Arg Val Leu Gly Ser Gly Ala Phe Gly Lys Val Val
                595                 600                 605
Glu Gly Thr Ala Tyr Gly Leu Ser Arg Ser Gln Pro Val Met Lys Val
        610                 615                 620
Ala Val Lys Met Leu Lys Pro Thr Ala Arg Ser Ser Glu Lys Gln Ala
625                 630                 635                 640
Leu Met Ser Glu Leu Lys Ile Met Thr His Leu Gly Pro His Leu Asn
                645                 650                 655
Ile Val Asn Leu Leu Gly Ala Cys Thr Lys Ser Gly Pro Ile Tyr Ile
            660                 665                 670
Ile Thr Glu Tyr Cys Phe Tyr Gly Asp Leu Val Asn Tyr Leu His Lys
        675                 680                 685
Asn Arg Asp Ser Phe Leu Ser His His Pro Glu Lys Pro Lys Lys Glu
            690                 695                 700
Leu Asp Ile Phe Gly Leu Asn Pro Ala Asp Glu Ser Thr Arg Ser Tyr
705                 710                 715                 720
Val Ile Leu Ser Phe Glu Asn Asn Gly Asp Tyr Met Asp Met Lys Gln
                725                 730                 735
Ala Asp Thr Thr Gln Tyr Val Pro Met Leu Glu Arg Lys Glu Val Ser
            740                 745                 750
Lys Tyr Ser Asp Ile Gln Arg Ser Leu Tyr Asp Arg Pro Ala Ser Tyr
        755                 760                 765
```

```
Lys Lys Lys Ser Met Leu Asp Ser Glu Val Lys Asn Leu Leu Ser Asp
    770                 775                 780

Asp Asn Ser Glu Gly Leu Thr Leu Leu Asp Leu Leu Ser Phe Thr Tyr
785                 790                 795                 800

Gln Val Ala Arg Gly Met Glu Phe Leu Ala Ser Lys Asn Cys Val His
                805                 810                 815

Arg Asp Leu Ala Ala Arg Asn Val Leu Leu Ala Gln Gly Lys Ile Val
            820                 825                 830

Lys Ile Cys Asp Phe Gly Leu Ala Arg Asp Ile Met His Asp Ser Asn
        835                 840                 845

Tyr Val Ser Lys Gly Ser Thr Phe Leu Pro Val Lys Trp Met Ala Pro
850                 855                 860

Glu Ser Ile Phe Asp Asn Leu Tyr Thr Thr Leu Ser Asp Val Trp Ser
865                 870                 875                 880

Tyr Gly Ile Leu Leu Trp Glu Ile Phe Ser Leu Gly Gly Thr Pro Tyr
                885                 890                 895

Pro Gly Met Met Val Asp Ser Thr Phe Tyr Asn Lys Ile Lys Ser Gly
            900                 905                 910

Tyr Arg Met Ala Lys Pro Asp His Ala Thr Ser Glu Val Tyr Glu Ile
        915                 920                 925

Met Val Lys Cys Trp Asn Ser Glu Pro Glu Lys Arg Pro Ser Phe Tyr
    930                 935                 940

His Leu Ser Glu Ile Val Glu Asn Leu Leu Pro Gly Gln Tyr Lys Lys
945                 950                 955                 960

Ser Tyr Glu Lys Ile His Leu Asp Phe Leu Lys Ser Asp His Pro Ala
                965                 970                 975

Val Ala Arg Met Arg Val Asp Ser Asp Asn Ala Tyr Ile Gly Val Thr
            980                 985                 990

Tyr Lys Asn Glu Glu Asp Lys Leu Lys Asp Trp Glu Gly Gly Leu Asp
        995                 1000                1005

Glu Gln Arg Leu Ser Ala Asp Ser Gly Tyr Ile Ile Pro Leu Pro Asp
    1010                1015                1020

Ile Asp Pro Val Pro Glu Glu Glu Asp Leu Gly Lys Arg Asn Arg His
1025                1030                1035                1040

Ser Ser Gln Thr Ser Glu Glu Ser Ala Ile Glu Thr Gly Ser Ser Ser
                1045                1050                1055

Ser Thr Phe Ile Lys Arg Glu Asp Glu Thr Ile Glu Asp Ile Asp Met
            1060                1065                1070

Met Asp Asp Ile Gly Ile Asp Ser Ser Asp Leu Val Glu Asp Ser Phe
        1075                1080                1085

Leu

<210> SEQ ID NO 2
<211> LENGTH: 6413
<212> TYPE: DNA
<213> ORGANISM: Artificial Sequence
<220> FEATURE:
<223> OTHER INFORMATION: Description of Artificial Sequence:/note =
      Synthetic Construct

<400> SEQUENCE: 2
ccattactgt tggagctaca gggagagaaa caggaggaga atgcaagaga tcatttggga      60
aggccgtggg cacgctcttt actccatgtg tgggacattc attgcggaat aacatcggag     120
gagaagtttc ccagagctat ggggacttcc catccggcgt tcctggtctt aggctgtctt     180
```

```
ctcacagggc tgagcctaat cctctgccag ctttcattac cctctatcct tccaaatgaa      240
aatgaaaagg ttgtgcagct gaattcatcc ttttctctga gatgctttgg ggagagtgaa      300
gtgagctggc agtaccccat gtctgaagaa gagagctccg atgtggaaat cagaaatgaa      360
gaaaacaaca gcggccttt tgtgacggtc ttggaagtga gcagtgcctc ggcggcccac       420
acagggttgt acacttgcta ttacaaccac actcagacag aagagaatga gcttgaaggc      480
aggcacattt acatctatgt gccagaccca gatgtagcct ttgtacctct aggaatgacg      540
gattatttag tcatcgtgga ggatgatgat tctgccatta taccttgtcg cacaactgat      600
cccgagactc ctgtaacctt acacaacagt gagggggtgg tacctgcctc ctacgacagc      660
agacagggct ttaatgggac cttcactgta gggccctata tctgtgaggc caccgtcaaa      720
ggaaagaagt tccagaccat cccatttaat gtttatgctt taaaagcaac atcagagctg      780
gatctagaaa tggaagctct taaaaccgtg tataagtcag gggaaacgat tgtggtcacc      840
tgtgctgttt ttaacaatga ggtggttgac cttcaatgga cttaccctgg agaagtgaaa      900
ggcaaaggca tcacaatgct ggaagaaatc aaagtcccat ccatcaaatt ggtgtacact      960
ttgacggtcc ccgaggccac ggtgaaagac agtggagatt acgaatgtgc tgcccgccag     1020
gctaccaggg aggtcaaaga aatgaagaaa gtcactattt ctgtccatga gaaaggtttc     1080
attgaaatca acccaccctt cagccagttg gaagctgtca acctgcatga agtcaaacat     1140
tttgttgtag aggtgcgggc ctacccacct cccaggatat cctggctgaa aaacaatctg     1200
actctgattg aaaatctcac tgagatcacc actgatgtgg aaaagattca ggaaataagg     1260
tatcgaagca aattaaagct gatccgtgct aaggaagaag acagtggcca ttatactatt     1320
gtagctcaaa atgaagatgc tgtgaagagc tatacttttg aactgttaac tcaagttcct     1380
tcatccattc tggacttggt cgatgatcac catggctcaa ctggggggaca gacggtgagg     1440 tgcacagctg aaggcacgcc gcttcctgat attgagtgga tgatatgcaa agatattaag     1500
aaatgtaata tgaaacttc ctggactatt ttggccaaca atgtctcaaa catcatcacg      1560
gagatccact cccgagacag gagtaccgtg gagggccgtg tgactttcgc caaagtggag     1620
gagaccatcg ccgtgcgatg cctggctaag aatctccttg gagctgagaa ccgagagctg     1680
aagctggtgg ctcccaccct gcgttctgaa ctcacggtgg ctgctgcagt cctggtgctg     1740
ttggtgattg tgatcatctc acttattgtc ctggttgtca tttggaaaca gaaaccgagg     1800
tatgaaattc gctggagggt cattgaatca atcagcccgg atggacatga atatatttat     1860
gtggacccga tgcagctgcc ttatgactca agatgggagt ttccaagaga tggactagtg     1920
cttggtcggg tcttgggtc tggagcgttt gggaaggtgg ttgaaggaac agcctatgga     1980
ttaagccggt cccaacctgt catgaaagtt gcagtgaaga tgctaaaacc cacggccaga     2040
tccagtgaaa aacaagctct catgtctgaa ctgaagataa tgactcacct ggggccacat     2100
ttgaacattg taaacttgct gggagcctgc accaagtcag gccccattta catcatcaca     2160
gagtattgct tctatggaga tttggtcaac tatttgcata agaatagggat agcttcctg     2220 agccaccacc cagagaagcc aaagaaagag ctggatatct ttggattgaa ccctgctgat     2280
gaaagcacac ggagctatgt tattttatct tttgaaaaca tggtgactaa catggacatg     2340
aagcaggctg atactacaca gtatgtcccc atgctagaaa ggaaagaggt ttctaaatat     2400
tccgacatcc agatcactct ctatgatcgt ccagcctcat ataagaagaa atctatgtta     2460
gactcagaag tcaaaaacct cctttcagat gataactcag aaggccttac tttattggat     2520
```

```
ttgttgagct tcacctatca agttgcccga ggaatggagt ttttggcttc aaaaaattgt   2580
gtccaccgtg atctggctgc tcgcaacgtc ctcctggcac aaggaaaaat tgtgaagatc   2640
tgtgactttg gcctgccag agacatcatg catgattcga actatgtgtc gaaaggcagt    2700
acctttctgc ccgtgaagtg gatggctcct gagagcatct tgacaaccct ctacaccaca   2760
ctgagtgatg tctggtctta tggcattctg ctctgggaga tctttccct tggtggcacc    2820 ccttacccg gcatgatggt ggattctact ttctacaata agatcaagag tgggtaccgg    2880
atggccaagc ctgaccacgc taccagtgaa gtctacgaga tcatggtgaa atgctggaac   2940
agtgagccga agaagagacc ctccttttac cacctgagtg agattgtgga gaatctgctg   3000
cctggacaat ataaaaagag ttatgaaaaa attcacctgg acttcctgaa gagtgaccat   3060
cctgctgtgg cacgcatgcg tgtggactca gacaatgcat acattggtgt cacctacaaa   3120
aacgaggaag acaagctgaa ggactgggag ggtggtctgg atgagcagag actgagcgct   3180
gacagtggct acatcattcc tctgcctgac attgaccctg ccctgagga ggaggacctg     3240 ggcaagagga acagacacag ctcgcagacc tctgaagaga gtgccattga cgggttcc      3300 agcagttcca ccttcatcaa gagagaggac gagaccattg aagacatcga catgatggac   3360
gacatcggca tagactcttc agacctggtg gaagacagct tcctgtaact ggcggattcg   3420
aggggttcct tccacttctg ggccaccctc tggatcccgt tcagaaaacc actttattgc   3480
aatgcggagg ttgagaggag gacttggttg atgtttaaag agaagttccc agccaagggc   3540
ctcggggagc gttctaaata tgaatgaatg ggatattttg aaatgaactt tgtcagtgtt   3600
gcctctcgca atgcctcagt agcatctcag tggtgtgtga agtttggaga tagatggata   3660
agggaataat aggccacaga aggtgaactt tgtgcttcaa ggacattggt gagagtccaa   3720
cagacacaat ttatactgcg acagaacttc agcattgtaa ttatgtaaat aactctaacc   3780
aaggctgtgt ttagattgta ttaactatct tctttggact tctgaagaga ccactcaatc   3840
catccatgta cttccctctt gaaacctgat gtcagctgct gttgaacttt ttaaagaagt   3900
gcatgaaaaa ccattttga acctaaaaag gtactggtac tatagcattt tgctatcttt     3960
tttagtgtta aagagataaa gaataataat taaccaacct tgtttaatag atttgggtca   4020
tttagaagcc tgacaactca tttttcatatt gtaatctatg tttataatac tactactgtt   4080
atcagtaatg ctaaatgtgt aataatgtaa catgatttcc ctccagagaa agcacaattt   4140
aaaacaatcc ttactaagta ggtgatgagt ttgacagttt ttgacattta tattaaataa   4200
catgtttctc tataaagtat ggtaatagct ttagtgaatt aaatttagtt gagcatagag   4260
aacaaagtaa aagtagtgtt gtccaggaag tcagaatttt taactgtact gaataggttc   4320
cccaatccat cgtattaaaa aacaattaac tgccctctga ataatggga ttagaaacaa     4380 acaaaactct taagtcctaa aagttctcaa tgtagaggca taaacctgtg ctgaacataa   4440
cttctcatgt atattaccca atggaaaata taatgatcag caaaaagact ggatttgcag   4500 aagtttttt tttttttctt catgcctgat gaaagctttg caaccccaa tatatgtatt      4560 ttttgaatct atgaacctga aagggtcag aaggatgccc agacatcagc ctccttcttt     4620 cacccctta cccaaagaga aagagtttga aactcgagac cataaagata ttctttagtg    4680
gaggctggat gtgcattagc ctggatcctc agttctcaaa tgtgtgtggc agccaggatg    4740
actagatcct gggtttccat ccttgagatt ctgaagtatg aagtctgagg gaaaccagag    4800
tctgtatttt tctaaactcc ctggctgttc tgatcggcca gttttcggaa acactgactt   4860
aggtttcagg aagttgccat gggaaacaaa taatttgaac tttggaacag ggttggaatt   4920
```

```
caaccacgca ggaagcctac tatttaaatc cttggcttca ggttagtgac atttaatgcc    4980
atctagctag caattgcgac cttaatttaa cttttccagtc ttagctgagg ctgagaaagc   5040
taaagtttgg ttttgacagg ttttccaaaa gtaaagatgc tacttcccac tgtatggggg   5100
agattgaact ttccccgtct cccgtcttct gcctcccact ccatacccccg ccaaggaaag  5160 gcatgtacaa aaattatgca attcagtgtt ccaagtctct gtgtaaccag ctcagtgttt   5220
tggtggaaaa aacattttaa gttttactga taatttgagg ttagatggga ggatgaattg   5280
tcacatctat ccacactgtc aaacaggttg gtgtgggttc attggcattc tttgcaatac   5340
tgcttaattg ctgataccat atgaatgaaa catgggctgt gattactgca atcactgtgc   5400
tatcggcaga tgatgctttg gaagatgcag aagcaataat aaagtacttg actacctact   5460
ggtgtaatct caatgcaagc cccaactttc ttatccaact ttttcatagt aagtgcgaag   5520
actgagccag attggccaat taaaaacgaa aacctgacta ggttctgtag agccaattag   5580
acttgaaata cgtttgtgtt tctagaatca cagctcaagc attctgttta tcgctcactc   5640
tcccttgtac agccttattt tgttggtgct ttgcattttg atattgctgt gagccttgca   5700
tgacatcatg aggccggatg aaacttctca gtccagcagt ttccagtcct aacaaatgct   5760
cccacctgaa tttgtatatg actgcatttg tgggtgtgtg tgtgttttca gcaaattcca   5820
gatttgtttc cttttggcct cctgcaaagt ctccagaaga aaatttgcca atctttccta   5880 cttctatt ttatgatgac aatcaaagcc ggcctgagaa acactatttg tgacttttta   5940
aacgattagt gatgtcctta aaatgtggtc tgccaatctg tacaaaatgg tcctatttt   6000 gtgaagaggg acataagata aaatgatgtt atacatcaat atgtatatat gtatttctat   6060
atagacttgg agaatactgc caaaacattt atgacaagct gtatcactgc cttcgtttat   6120 attttttttaa ctgtgataat ccccacaggc acattaactg ttgcacttt gaatgtccaa   6180 aatttatatt ttagaaataa taaaaagaaa gatacttaca tgttcccaaa acaatggtgt   6240
ggtgaatgtg tgagaaaaac taacttgata gggtctacca atacaaaatg tattacgaat   6300
gcccctgttc atgtttttgt tttaaaacgt gtaaatgaag atctttatat ttcaataaat   6360
gatatataat ttaaagttaa aaaaaaaaaa aaaaaaaaaa aaaaaaaaaa aaa          6413
```